US005856126A

United States Patent [19]

Fukuchi et al.

[11] Patent Number: 5,856,126

[45] Date of Patent: Jan. 5, 1999

[54] PEPTIDE HAVING ANTI-THROMBUS ACTIVITY AND METHOD OF PRODUCING THE SAME

[75] Inventors: Naoyuki Fukuchi; Hiroshi Yamamoto; Mitsuyo Nagano; Morikazu Kito; Akiko Tanaka; Koichi Ishii; Tsuyoshi Kobayashi; Ryota Yoshimoto, all of Kawasaki, Japan

[73] Assignee: Ajinomoto Co., Inc., Tokyo, Japan

[21] Appl. No.: 612,840

[22] PCT Filed: Sep. 21, 1994

[86] PCT No.: PCT/JP94/01555

§ 371 Date: Mar. 20, 1996

§ 102(e) Date: Mar. 20, 1996

[87] PCT Pub. No.: WO95/08573

PCT Pub. Date: Mar. 30, 1995

[30] Foreign Application Priority Data

Sep. 22, 1993 [JP] Japan .................................... 5-236975

[51] Int. Cl.[6] ......................... C07K 14/435; C07K 14/46; C12N 15/12; A61K 38/16

[52] U.S. Cl. ........................... 435/69.1; 514/12; 514/822; 530/350; 530/856; 530/402; 536/23.5; 435/440

[58] Field of Search ................................ 435/69.1, 172.3, 435/320.1, 252.3, 440, 325, 402; 514/2, 21, 822; 530/350, 856

[56] References Cited

U.S. PATENT DOCUMENTS

| | | | |
|---|---|---|---|
| 5,336,667 | 8/1994 | Kirby | 514/12 |
| 5,342,830 | 8/1994 | Scarborough | 514/12 |
| 5,679,542 | 10/1997 | Scarborough | 435/69.1 |

FOREIGN PATENT DOCUMENTS

| | | |
|---|---|---|
| 2-234692 | 9/1990 | Japan . |
| 4-144695 | 5/1992 | Japan . |
| WO 92/08472 | 5/1992 | WIPO . |
| WO 93/11151 | 10/1993 | WIPO . |

OTHER PUBLICATIONS

T.E. Creighton, “Protein Structure a Practical Approach”, 1989, IRL Press at Oxford University Press, pp. 155–159.

Yoshihiro Fujimura et al, “Snake Venom Proteins Modulating the Interaction Between von Willebrand Factor and Platelet Glycoprotein lb”, 1996, F.K. Schattauer Verlagsgesellschaft mbH (Stuttgart) 76 (5), pp. 633–639.

W. W. Cleland, “Dithiothreitol, A New Protective Reagent For SH Groups”, Nov. 4, 1963, From the Department of Biochemistry, University of Wisconsin, Madison, pp. 480–482.

H. Fraenkel–Conrat et al, “The Molecular Weight of Lysozyme After Reduction and Alkylation of the Disulfide Bonds”, Feb. 1951, vol. 73, pp. 625–627.

Thomas A. Bewley et al, “Human Pituitary Growth Hormone. XVI. Reduction With Dithiothreitol in the Absence of Urea”, 1968, Biochim. Biophys. Acta, 154, pp. 420–422.

Robert K. Andrews, “Binding of a Novel 50–Kilodalton Alboaggregin From Trimeresurus Albolabris and Related Viper Venom Proteins to the Platelet Membrane Glycoprotein Lb–IX–V Complex. Effect On Platelet Aggregation and Glycoprotein Ib–Mediated Platelet Activation”, 1996, Biochemistry, vol. 35, 12629–12639.

Peng, M. et al. *Blood* 81(9):2321–2328 (1993).

*Primary Examiner*—Dian C. Jacobson

*Attorney, Agent, or Firm*—Oblon, Spivak, McClelland, Maier & Neustadt, P.C.

[57] ABSTRACT

A multimer peptide from a snake venom has an activity to inhibit binding between von Willebrand factor and platelets. The multimer peptide is used to obtain a single strand peptide which does not substantially cause decrease in platelets at a minimum dose for exhibiting the activity in vivo. The single strand peptide is obtained by allowing the multimer peptide to exist together with a protein-denaturing agent, and glutathione and/or cysteine, and thereby disconnecting disulfide bonds between peptide chains for constituting the multimer peptide while substantially preserving disulfide bonds within the peptide chains. Alternatively, the single strand peptide, a mutant thereof, or a part thereof is produced by genetic engineering techniques by using genes coding for them.

26 Claims, 25 Drawing Sheets

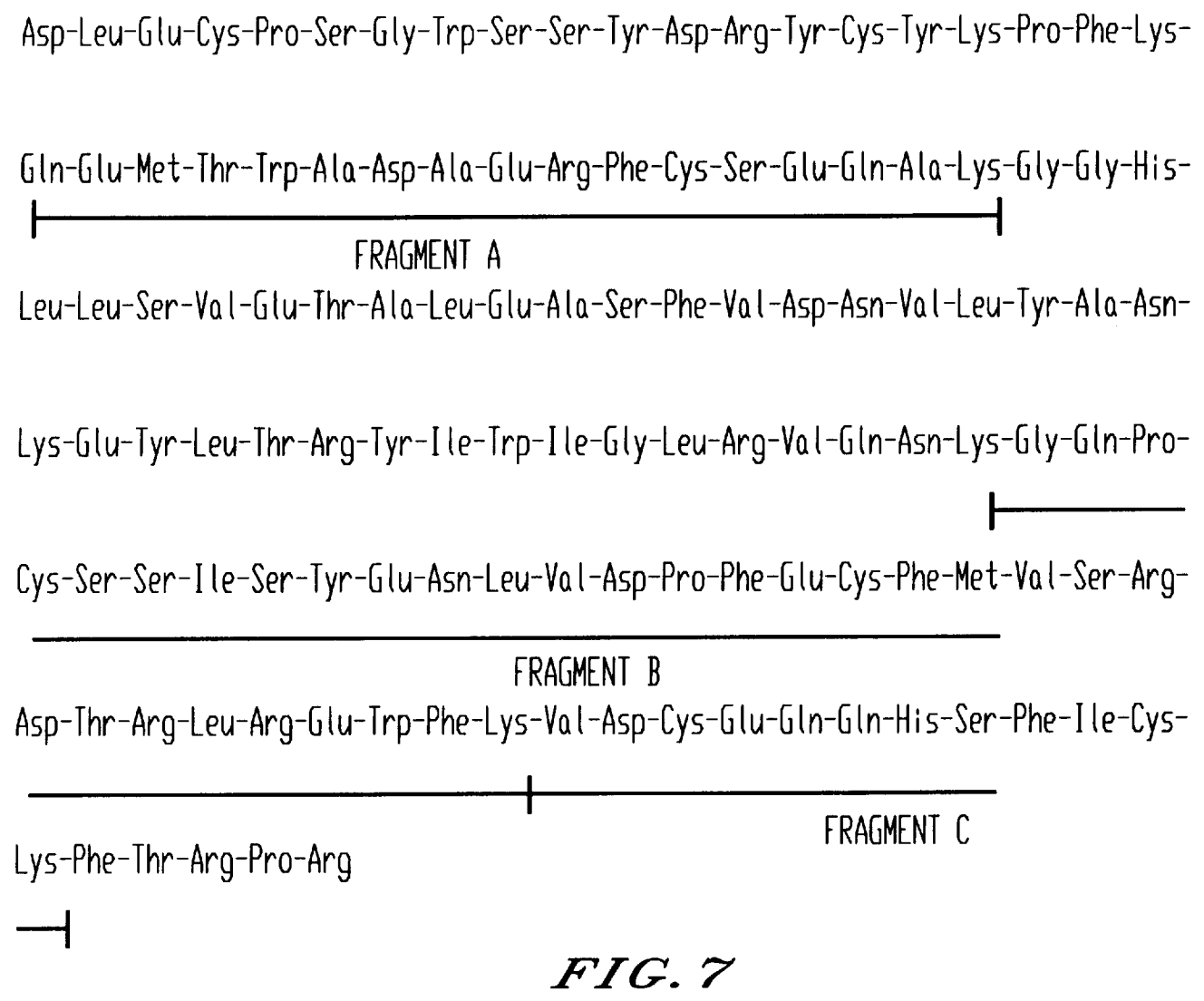

Asp-Leu-Glu-Cys-Pro-Ser-Gly-Trp-Ser-Ser-Tyr-Asp-Arg-Tyr-Cys-Tyr-Lys-Pro-Phe-Lys-

Gln-Glu-Met-Thr-Trp-Ala-Asp-Ala-Glu-Arg-Phe-Cys-Ser-Glu-Gln-Ala-Lys-Gly-Gly-His-

FRAGMENT A

Leu-Leu-Ser-Val-Glu-Thr-Ala-Leu-Glu-Ala-Ser-Phe-Val-Asp-Asn-Val-Leu-Tyr-Ala-Asn-

Lys-Glu-Tyr-Leu-Thr-Arg-Tyr-Ile-Trp-Ile-Gly-Leu-Arg-Val-Gln-Asn-Lys-Gly-Gln-Pro-

Cys-Ser-Ser-Ile-Ser-Tyr-Glu-Asn-Leu-Val-Asp-Pro-Phe-Glu-Cys-Phe-Met-Val-Ser-Arg-

FRAGMENT B

Asp-Thr-Arg-Leu-Arg-Glu-Trp-Phe-Lys-Val-Asp-Cys-Glu-Gln-Gln-His-Ser-Phe-Ile-Cys-

FRAGMENT C

Lys-Phe-Thr-Arg-Pro-Arg

*FIG. 7*

INHIBITION ON RISTOCETION-INDUCED AGGREGATION(%)

INHIBITION ON BOTROCETION-INDUCED AGGREGATION(%)

PEPTIDE HAVING ANTI-THROMBUS ACTIVITY AND METHOD OF PRODUCING THE SAME

TECHNICAL FIELD

The present invention relates to a peptide having anti-thrombus activity, a method of producing the peptide, and a pharmaceutical composition containing the peptide. In particular, the present invention relates to a peptide originating from a snake venom, the peptide not causing decrease in platelets or thrombocytes (thrombocytopenia) in vivo.

BACKGROUND ART

It is widely known that platelets closely participate in crisis of so-called thrombosis represented by myocardial infarction and cerebral thrombosis ("Platelets", edited by Yamanaka and Yamazaki, Igaku-Syoin, pp. 158–163 (1991)). Recently, it has been reported that the binding between von Willebrand factor as one of blood proteins and glycoprotein Ib located on platelet surfaces is important for platelets to adhere to intravascular subendotherial tissue, which is considered as an early reaction to cause thrombosis (J. P. Cean et al., *J. Lab. Clin. Med.,* 87, 586–596 (1976)).

It is known that the binding between the two species of the proteins does not occur in an ordinary state, but it occurs only when a high shear stress is exerted in vivo (T. T. Vincent et al., *Blood,* 65, 823–831 (1985)). The methodology to observe the binding exo-vivo includes a widely spread method which uses certain substances such as ristocetin as an antibiotic (M. A. Howard, B. G. Firkin, *Thromb. Haemostatis,* 26, 362–369 (1971)) and botrocetin as a protein originating from a snake venom (M. S. Read et al., *Proc. Natl. Acad. Sci. U.S.A.,* 75, 4514–4518 (1978)). Platelet aggregation occurs when these substances are added to a suspension of platelets. These aggregation depends on the binding between von Willebrand factor and glycoprotein Ib (M. A. Howard, B. G. Firkin, M. S. Read et al., supra).

Several compounds have been already reported, which exhibit an inhibiting action on the platelet aggregation mediated by ristocetin or botrocetin. Such known compounds include, for example, aurintricarboxylic acid (M. D. Phillips et al., *Blood,* 72, 1989–1903 (1988)), and dye substances such as aromatic amidino compounds (J. D. Geratz et al., *Thromb. Haemostasis,* 39, 411–425 (1978)), as well as partial fragment peptides of von Willebrand factor or glycoprotein Ib (Y. Fujimura et al., *J. Biol. Chem.,* 261, 381–385 (1986); K. Titani et al., *Proc. Natl. Acad. Sci. U.S.A.,* 84, 5610–5614 (1987)).

It has been also reported that peptides having similar platelet aggregation-inhibiting activities are present in snake venoms. An international publication pamphlet of WO9208472 describes such peptides from *Crotalus horridus horridus* and *Cerastes cerastes*, each peptide comprising two different strands having a molecular weight of about 25 kilodaltons in which the homology is high at least in amino acid sequences on N-terminal side. A platelet aggregation-inhibiting peptide, which has been reported by Peng et al. (M. Peng et al., *Blood,* 81, 2321–2328 (1993)) as obtained from *Echis carinatus,* is also extremely similar to the peptides described above in its in vitro activity, molecular weight, etc. Any of the platelet aggregation-inhibiting peptides originating from snake venoms inhibits platelet aggregation mediated by ristocetin or botrocetin at a low concentration of 2 to 5 μg/ml or less in vitro.

The international publication pamphlet of WO9208472 does not describes the anti-thrombus activity upon administration to animals. Accordingly, as described in Example 1 in this specification, the present inventors purified a peptide having equivalent properties to the peptide described in the pamphlet, considering a purification method for the peptide originating from *Crotalus horridus horridus* described in the pamphlet, in order to investigate the action upon administration to animals. As a result, the present inventors observed almost complete disappearance of platelets in blood upon administration in a small amount of 100 μg/kg. However, the international publication pamphlet of WO9208472 describes neither suggestion nor solution of such a problem upon administration to animals.

Moreover, the peptide from *Echis carinatus* obtained by Peng et al. has its molecular weight of about 26 kilodaltons under a non-reduced condition as measured by SDS-polyacrylamide gel electrophoresis, while the peptide provides two peptides of about 14 kilodaltons and about 16 kilodaltons under a reduced condition. Accordingly, it is postulated that this peptide is also homologous to the peptide originating from *Crotalus horridus horridus.* It has been also reported for this peptide that remarkable decrease in platelets is observed upon administration to animals (M. Peng et al., *Blood,* 81, 2321–2328 (1993)).

The respective peptides originating from snake venoms, which inhibit the binding between von Willebrand factor and platelets, have high homology in their amino acid sequences, and they are also extremely similar in their molecular weights. In addition, according to the result described above, it is assumed that these peptides also have an activity to cause decrease in platelets in vivo. Namely, these peptides inhibit the binding of von Willebrand factor with platelets in vitro at a low concentration, however, they are difficult to be utilized as an anti-thrombosis drug for in vivo administration. The present inventors have considered the mechanism to cause the decrease in platelets as follows.

The peptides from snake venoms, which inhibit platelet aggregation mediated by ristocetin or botrocetin at a low concentration, have, for example, an amino acid sequence as described in the international publication pamphlet of WO9208472. According to the amino acid sequence, the peptide from snake venom conserves approximate positions of cysteine residues and a part of a sequence considered to be necessary for the lectin activity (W. I. Weis et al., *Science,* 254, 1608–1615 (1991)), as compared with a peptide having a calcium-dependent lectin activity reported by Drickamer et al. and referred to as "C-type lectin" (K. Drickamer, *J. Biol. Chem.,* 263, 9557–9560 (1988)).

Other than the above, peptides having high homology to the C-type lectin in their amino acid sequences have been obtained from snake venoms, including, for example, botrocetin obtained from *Botrops jararaca* (Y. Usami et al., *Proc. Natl. Acad. Sci. U.S.A.,* 90, 928–932 (1993)), rattle snake lectin obtained from *Crotalus atrox* (J. Hirabayashi et al., *J. Biol. Chem.,* 266, 2320–2326 (1991)), and alboaggregin obtained from *Trimeresurus albolabris* (E. Yoshida et al., *Biochem. Biophys. Res. Commun.,* 191, 1386–1392 (1993)).

These peptides also conserve approximate positions of cysteine residues and a part of the sequence considered to be necessary for the lectin activity, as compared with C-type lectin. It is also known that C-type lectin has an activity to agglutinate cells, bacteria and so on through glycoproteins (sugar chains) on their cell membranes (K. Drickamer, J. Hirabayashi et al., supra).

When the platelet-aggregation is measured in vitro, collected blood samples are often added with citric acid, sodium citrate, and ethylenediaminetetraacetic acid (EDTA)

as anticoagulants, and hence calcium is chelated in such a platelet aggregation-measuring system. Accordingly, calcium-dependent reactions are inhibited. For this reason, it is difficult to detect in vitro whether or not the peptides from snake venoms exhibiting the platelet aggregation-inhibiting activity have the lectin activity.

Thus it is considered that the peptides from snake venoms express the C-type lectin activity in the presence of calcium in vivo upon administration to animals, and they cause aggregation of platelets. It is assumed that such an action is one of factors to cause the observed phenomena such as collection of platelet aggregates in microvessels, and consequent decrease in platelets or thrombocytes (thrombocytopenia).

Therefore, in order that the peptide from snake venom which inhibits the binding of von Willebrand factor with platelets functions as an anti-thrombosis drug which is efficacious in vivo such as in experiments with animals, it is necessary to obtain a new active peptide prepared by conversion into a molecule which does not cause decrease in platelets.

DISCLOSURE OF THE INVENTION

The present invention has been made from the viewpoint described above, an object of which is to provide a peptide which inhibits the binding of von Willebrand factor with platelets without causing the decrease in platelets, and a method of producing the peptide, in order to obtain a drug which is efficacious as an anti-thrombosis drug.

As a result of diligent studies in order to achieve the object described above, the present inventors have found that a single strand peptide, which is obtained by dissociating a multimer peptide from a snake venom under a certain condition, has an anti-thrombus activity without causing any decrease in platelets upon in vivo administration. Thus the present invention has been completed.

Namely, the present invention lies in a single strand peptide obtained by disconnecting disulfide bonds between peptide chains for constituting a multimer peptide from a snake venom having an activity to inhibit binding between von Willebrand factor and platelets while substantially preserving disulfide bonds within said peptide chains, wherein the single strand peptide (hereinafter referred to as "peptide of the present invention" or "active peptide", if necessary) does not substantially cause decrease in platelets at a minimum dose for exhibiting the activity in vivo.

In another aspect, the present invention provides a method of producing a single strand peptide obtainable from a multimer peptide from a snake venom having an activity to inhibit binding between von Willebrand factor and platelets, wherein the single strand peptide does not substantially cause decrease in platelets at a minimum dose for exhibiting the activity in vivo, the method comprising the steps of allowing the multimer peptide from the snake venom to exist together with a protein-denaturing agent, glutathione and/or cysteine, and thereby disconnecting disulfide bonds between peptide chains for constituting the multimer peptide while substantially preserving disulfide bonds within the peptide chains.

In still another aspect, the present invention provides a method of producing a peptide which does not substantially cause decrease in platelets at a minimum dose for exhibiting an activity to inhibit binding between von Willebrand factor and platelets in vivo, the method comprising the steps of cultivating, in an appropriate medium, *Escherichia coli* transformed with a vector containing an inserted DNA fragment coding for the peptide or a part thereof, expressing the peptide, allowing the peptide accumulated in cells of *Escherichia coli* to exist together with a protein-denaturing agent, and then generating disulfide bonds within chains of the peptide by removing the protein-denaturing agent or by decreasing concentration of the protein-denaturing agent.

In still another aspect, the present invention provides a method of producing a peptide which does not substantially cause decrease in platelets at a minimum dose for exhibiting an activity to inhibit binding between von Willebrand factor and platelets in vivo, the method comprising the steps of cultivating, in an appropriate medium, cultured insect cells or cultured animal cells transformed with a vector containing an inserted DNA fragment coding for the peptide or a part thereof, expressing the peptide, and recovering the peptide accumulated in the cells or in the medium.

In still another aspect, the present invention provides a pharmaceutical composition containing an efficacious component of the peptide and/or a pharmaceutically acceptable salt thereof.

It is noted that the term "peptide" simply referred to in this specification indicates the single strand peptide in some cases, while the term indicates the multimer peptide in other cases.

The present invention will be described in detail below.

<1> The Peptide of the Present Invention

The peptide of the present invention is a single strand peptide obtained by disconnecting disulfide bonds between peptide chains for constituting the multimer peptide from a snake venom having the activity to inhibit the binding between von Willebrand factor and platelets while substantially preserving disulfide bonds within said peptide chains. The peptide of the present invention is further characterized in that it does not substantially exhibit the decrease in platelets or thrombocytes (thrombocytopenia) at a minimum dose for exhibiting the activity in vivo.

The present invention is applicable to any multimer peptide from the snake venom provided that the multimer peptide has the activity to inhibit the binding between von Willebrand factor and platelets. The multimer peptide includes, for example, peptides originating from snake venoms produced by *Crotalus horridus horridus, Cerastes cerastes, Echis carinatus, Trimeresurus albolabris,* and *Vipera palaestina.* Among them, a peptide from a snake venom produced by *Crotalus horridus horridus* is preferred.

Specifically, the peptide of the present invention is represented by a single strand peptide obtained from the snake venom peptide originating from *Crotalus horridus horridus,* including those having an amino acid sequence shown in SEQ ID NO: 1 in Sequence Listing at their N-terminals. The peptide of the present invention also includes peptides having an amino acid sequence shown in SEQ ID NO: 2 in Sequence Listing, and comprising disulfide bonds between 4th and 15th cysteine residues, between 32th and 120th cysteine residues, and between 95th and 112th cysteine residues as counted from the N-terminal in SEQ ID NO: 2. The peptide can be also produced by using genetic engineering techniques. In such production, a methionine residue corresponding to a translation initiation codon is occasionally added to the N-terminal of the amino acid sequence shown in SEQ ID NO: 1 or 2 in Sequence Listing. The peptide of the present invention also includes peptides with the methionine residue added at the N-terminal as described above.

It is also possible to produce peptides which have the activity described above and have the amino acid sequence shown in SEQ ID NO: 2 in Sequence Listing or a part thereof by using, for example, *Escherichia coli*, cultured insect cells, or cultured animal cells in accordance with known genetic engineering techniques. When the peptide of the present invention is expressed by using *Escherichia coli* as a host, inclusion bodies are formed in cells. However, a peptide having the activity is obtained by solubilizing the inclusion bodies, and forming disulfide bonds correctly. In such a procedure, any cysteine residue, which does not participate in formation of the disulfide bond, may be substituted with an amino acid other than cysteine such as alanine or serine. Thus it is expected to avoid occurrence of erroneous disulfide bond formation, and improve the stability of an obtainable peptide. The amino acid sequence shown in SEQ ID NO: 2 includes amino acids or regions which are not necessary for the activity. It is also possible to construct peptides with substitution, deletion, or insertion at such one or more amino acids. For example, the activity is maintained even when 15 amino acid residues or 65 amino acid residues at the N-terminal and/or 11 amino acid residues at the C-terminal are deleted from the peptide having the amino acid sequence shown in SEQ ID NO: 2, as demonstrated in Example 6 described below.

Site-directed nucleotide sequence mutants can be prepared by using a commercially available kit (for example, Mutan-G and Mutan-K produced by Takara Shuzo). Alternatively, mutants can be also obtained by utilizing the PCR process as described in "PCR protocols" (published by Academic Press).

The single-stranded peptide of the present invention as described above does not substantially cause the decrease in platelets which would be caused by the multimer peptide, while maintaining the activity to inhibit the binding between von Willebrand factor and platelets. The peptide of the present invention having such properties exhibits the anti-thrombus activity in vivo, and it is useful as an anti-thrombosis drug.

<2> Method of Producing the Peptide of the Present Invention

For example, the following method is conceivable as one of means for obtaining, from the snake venom peptide, the peptide which does not cause the decrease in platelets while maintaining the activity to inhibit the binding between von Willebrand factor and platelets.

Assuming that the decrease in platelets upon administration of the snake venom peptide, which occurs in vivo, results from, among other things, a cause of the lectin activity of the snake venom peptide capable of appearing in the presence of calcium, it is considered that the activity to cross-link platelets disappears by separating sites from each other which correspond to sugar-binding sites existing in the lectin molecule. In order to separate such sugar-binding sites, for example, the multimer peptide may be disconnected into individual single strand chains.

In order to divide the multimer peptide into single strand chains, there are well-known methods including, for example, reduction of multimer peptides, or reduction of multimer peptides followed by protection and stabilization of free thiol groups of cysteine residues by means of carboxymethylation, carboxyamidomethylation, or pyridylethylation. However, in general, water-soluble proteins have a higher-order structure in which side chains of major hydrophilic amino acid residues are directed to the outside. Such a tertiary structure is destroyed by a strong denaturing condition, and a secondary structure is destroyed by reduction to cleave disulfide bonds between cysteine residues, or by protection of free thiol groups of cysteine residues after reduction, sometimes resulting in insolubilization in water.

As demonstrated in Example 1 described below, a double strand peptide obtained from *Crotalus horridus horridus* was changed into a peptide scarcely soluble in water on account of reducing carboxyamidomethylation, reducing pyridylmethylation, reduction with mercaptoethanol, etc.

Peng et al. (M. Peng et al., *Blood,* 81, 2321–2328 (1993)) has reported that a reaction mixture prepared by reduction of a double strand peptide obtained from *Echis carinatus* followed by carboxyamidomethylation also has a platelet aggregation-inhibiting activity similar to that of the double strand peptide. However, it is not reported at all whether or not the inhibition on aggregation is specific, or what produced molecule exhibits the activity.

Accordingly, in the present invention, the peptide from a snake venom is gently reduced under a mild denaturing condition without causing serious destruction of its higher-order structure. Thus disulfide bonds in the single strand chain of the double strand peptide, i.e. intramolecular disulfide bonds are substantially preserved, while disulfide bonds between the chains, i.e. intermolecular disulfide bonds are disconnected. Consequently, the single strand peptide is obtained which is highly water-soluble, and maintains the original higher-order structure at least at an extent that the peptide does not lose the activity.

In the present invention, the active peptide can be produced by using the multimer peptide contained in a snake venom which inhibits the binding of von Willebrand factor with platelets. For example, the active peptide is produced from a venom of *Crotalus horridus horridus*, or from a peptide obtained from a lyophilized product of the venom. It is noted that the inhibition on the binding of von Willebrand factor with platelets can be determined on the basis of inhibition on platelet aggregation induced by ristocetin or botrocetin (hereinafter simply referred to as "ristocetin-induced aggregation" or "botrocetin-induced aggregation", if necessary.

Means for disconnecting disulfide bonds between peptide chains to provide single strand chains while maintaining disulfide bonds between cysteine residues within the peptide chain include a method in which the multimer peptide is reacted by allowing it to exist together with a protein-denaturing agent, glutathione and/or cysteine. Guanidine hydrochloride, urea, etc. are used as the protein-denaturing agent. The final concentration of guanidine hydrochloride is from 0.01M to a saturated concentration. Preferably, guanidine hydrochloride is used in a concentration range of 1M to 6M. Glutathione and/or cysteine is used to perform reduction under a mild condition. When they are used, they are appropriately added in a concentration range of 0.1 mM to 100 mM, preferably 1 mM to 50 mM.

The reaction is performed in a buffer containing Tris-salt, phosphate salt, acetate salt, etc., in distilled water, or in a solution prepared by adding organic solvent such as alcohol to any of them. The reaction is performed in a state of solution in a temperature range of −10° C. to 100° C., preferably 10 ° C. to 40° C. Thus the objective single strand peptide can be obtained. The single strand peptide can be also obtained by performing a freezing and thawing treatment.

The active peptide produced as described above can be isolated by combining various methods such as gel filtration, ion exchange, adsorption, and reverse phase column chromatography, affinity column chromatography, ultrafiltration, electrophoresis, and countercurrent distribution.

Alternatively, the peptide of the present invention can be produced by using microorganisms or cultured cells by utilizing genetic recombination techniques for handling genes coding for the peptide. The gene coding for the peptide of the present invention is obtained by screening based on hybridization with a DNA fragment deduced from a part of the amino acid sequence for searching through a cDNA library obtained from a venom gland of *Crotalus horridus horridus* or a genomic DNA library obtained from a tissue, or by screening based on expressed proteins obtained from transformed cells allowed to express DNA included in the library, the transformed cells including, for example, prokaryotes represented by *Escherichia coli*, fungi such as yeast, and cultured cells such as those of insects and animals. It is also possible to combine and synthesize DNA sequences designed by using codons corresponding to respective amino acids, and appropriate regulator sequences, with reference to the amino acid sequence of the peptide of the present invention.

A clone having cDNA coding for the peptide of the present invention can be selected, for example, by extracting total RNA from a venom gland of *Crotalus horridus horridus*, purifying a mRNA fraction, synthesizing cDNA by using the mRNA as a template, preparing a cDNA library by using phage or the like, and conducting hybridization by using the cDNA library with an oligonucleotide probe prepared on the basis of the amino acid sequence of the peptide of the present invention. Alternatively, it is also available to use, as a probe for hybridization, a DNA fragment amplified from mRNA in accordance with the RT-PCR method by using oligonucleotide primers prepared on the basis of the amino acid sequence of the peptide of the present invention.

*E. coli* HB101/pCHA1 (*E. coli* AJ13023), which harbors a plasmid pCHA1 containing a gene coding for the peptide of the present invention obtained in Example described below, has been internationally deposited under a deposition number of FERM BP-4781 based on the Budapest Treaty since Aug. 12, 1994 in National Institute of Bioscience and Human Technology of Agency of Industrial Science and Technology of Ministry of International Trade and Industry (postal code: 305, 1–3 Higashi-Icchome, Tsukuba-shi, Ibaraki-ken, Japan).

The objective peptide can be expressed and produced under an appropriate condition by inserting the obtained gene into a plasmid or virus vector DNA containing a promoter, a translation initiation signal and so on expressible in a host, and performing introduction of the plasmid, or infection with the virus with respect to prokaryotes represented by *Escherichia coli*, fungi such as yeast, and cultured cells such as those of insects and animals. In this embodiment, the objective peptide can be accumulated in microbial cells or cultured cells, or it can be produced and secreted into a culture liquid. The objective peptide can be directly expressed in a form in which methionine as a translation initiation codon is added thereto. Alternatively, the objective peptide can be expressed in a form in which a secretion signal sequence is added. The objective peptide can be produced by cleaving and removing the signal sequence during secretion process. In another embodiment, the objective peptide may be expressed as a chimeric protein fused with another appropriate protein (for example, *Escherichia coli* maltose binding protein). In such an embodiment, the objective protein can be obtained by cleavage with an appropriate protease or with a chemical method after expressing the chimeric protein. When the protein thus expressed and produced does not have the objective activity due to a state of its higher-order structure, or when the protein only has a weak activity, it can be changed to form a higher-order structure having a sufficient activity by means of a treatment under an appropriate denaturing condition or under an appropriate oxidation-reduction condition.

When the peptide of the present invention is produced by using *Escherichia coli* as a host, the produced peptide forms inclusion bodies in cells as described above. However, the peptide having the activity can be obtained by solubilizing the inclusion bodies, and forming disulfide bonds correctly. Specifically, the peptide of the present invention is obtained by cultivating, in an appropriate medium, *Escherichia coli* transformed with a vector containing an inserted DNA fragment coding for the peptide of the present invention or a part thereof, expressing the peptide, allowing the peptide accumulated in cells of *Escherichia coli* to exist together with a protein-denaturing agent, and then generating disulfide bonds within chains of the peptide by removing the protein-denaturing agent or by decreasing concentration of the protein-denaturing agent. The disulfide bonds are formed, for example, between 4th and 15th cysteine residues, between 32th and 120th cysteine residues, and between 95th and 112th cysteine residues in SEQ ID NO: 2 when the peptide has the amino acid sequence shown in SEQ ID NO: 2.

Alternatively, the peptide of the present invention is obtained by cultivating, in an appropriate medium, cultured insect cells or cultured animal cells transformed with a vector containing an inserted DNA fragment coding for the peptide or a part thereof, expressing the peptide, and recovering the peptide accumulated in the cells or in the medium.

<3> Pharmaceutical Composition of the Present Invention

The peptide obtained as described above does not cause the decrease in platelets even after administration to animals. In fact, it remarkably inhibited thrombus formation after administration to thrombosis model animals.

Except for the dye substance such as Aurin tricarboxylic acid which has the property to non-specifically adsorb to proteins, the present invention has disclosed the substance for the first time that exhibits the anti-thrombus activity in vivo based on the feature that the binding of von Willebrand factor with platelets is inhibited. Namely, the present invention has revealed the fact for the first time that the activity to inhibit the binding of von Willebrand factor with platelets exists in the single strand peptide obtained from the peptide originating from a snake venom by using the method such as reduction. Thus the present invention provides a pharmaceutical composition which is extremely hopeful as an anti-thrombosis drug that does not cause the decrease in platelets upon administration in vivo.

The pharmaceutical composition of the present invention contains the peptide of the present invention and/or a pharmaceutically acceptable salt thereof as an active ingredient. A mixture of one or more species of the peptides of the present invention may be used. In one embodiment, the composition may contain substances having any anti-thrombosis function other than the peptide of the present invention. In such an embodiment, the peptide of the present invention is not necessarily a major component of the pharmaceutical composition. The composition may be blended with other materials ordinarily used as components for drug preparation including, for example, proteins such as serum albumin, salts for buffering action or osmotic pressure adjustment, carriers, and excipients.

The type of drug includes, for example, tablet, capsule, granule, syrup, suppository, ointment, injection, and instillation. Among them, injection drugs are preferred. The method of administration may be any of intravenous, subcutaneous, oral, ophthalmic, transintestinal administrations, etc. Among them, intravenous administration is preferred.

As for the dose upon administration to animals or human, an intended effect can be usually expected in a range of 0.1 μg/kg to 100 mg/kg, as an amount of the peptide of the present invention and/or the pharmaceutically accepted salt thereof. Within this range, it is possible to select an amount with which the most excellent medicinal effect is obtained.

BRIEF DESCRIPTION OF THE DRAWINGS

FIG. 7 shows an amino acid sequence of AS1051. Fragments A, B, C were obtained as one fragment connected through disulfide bonds by lysylendopeptidase digestion.

BEST MODE FOR CARRYING OUT THE INVENTION

Figure 1:
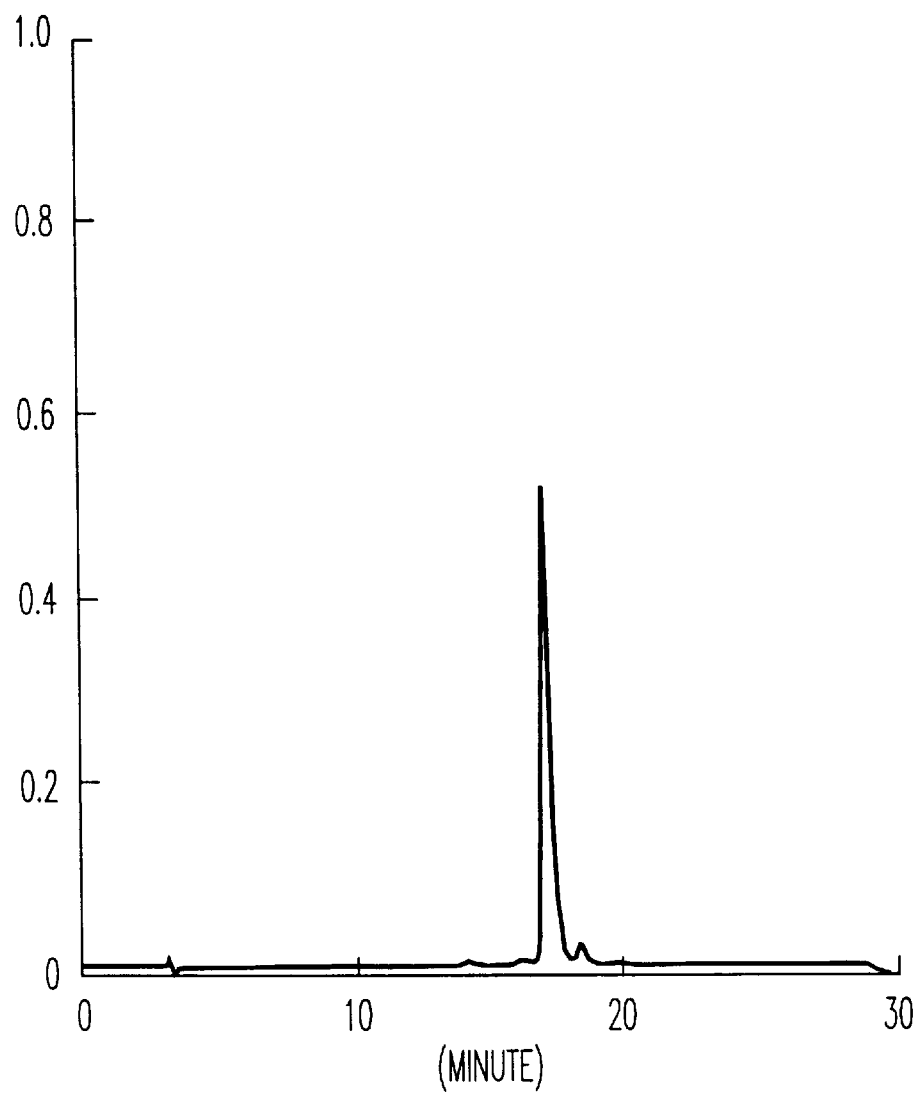
FIG. 1 shows a reverse phase chromatogram of CH-1.

Examples of the present invention will be described below.

EXAMPLE 1

Preparation of Anti-Thrombus Single Strand Peptide from *Crotalus horridus horridus*

<1> Preparation of Peptide Having Activity to Inhibit Binding of von Willebrand Factor with Platelets from *Crotalus horridus horridus*

A peptide having an activity to inhibit binding of von Willebrand factor with platelets was purified from a snake venom originating from *Crotalus horridus horridus* by using an index of an activity to inhibit ristocetin-mediated aggregation in accordance with a method described below.

Fresh blood collected from healthy human added with 1/10 volume of 3.8% sodium citrate was centrifuged at 900 rpm for 15 hours to obtain human platelet rich plasma to which an equal volume of physiological saline solution containing 2% paraformaldehyde was added, followed by being stored at 4° C. overnight stationarily. After the storage, platelets were recovered by centrifugation, and they were washed twice with a physiological saline solution containing 20 mM phosphate buffer (pH 7.4). A sample for measurement was added to a formalin-fixed platelet solution thus prepared, to which human plasma (final concentration: 0.12%) and ristocetin sulfate (produced by Sigma, final concentration: 0.5 mg/ml) were successively added. After shaking and agitation, the presence or absence of the inhibiting activity on platelet aggregation was observed macroscopically. The reaction solution had a volume of 50 μl. The sample was properly diluted, and added in an appropriate amount of 2 to 20 μl.

A lyophilized snake venom product (1 g) from *Crotalus horridus horridus* (produced by Sigma) was dissolved in a physiological saline solution (10 ml) containing 20 mM Tris-HCl (pH 7.4). Insoluble matters were removed by centrifugation at 3,000 rpm for 10 minutes. A supernatant was subjected to gel filtration chromatography by using the same buffer as a solvent and using a Sephadex G-75 (fine) (produced by Pharmacia) column (diameter: 5.0 cm, length: 90 cm) to make fractionation into fraction tubes. A fraction corresponding to an elution volume from 750 ml to 885 ml was collected, and divided into aliquots. Three aliquots, each having a volume of 15 ml, were allowed to pass through a benzamidine Sepharose (produced by Pharmacia) column (diameter 1.6 cm, length 5 cm) to collect a non-adsorbed fraction.

This fraction was filtrated and concentrated by using an ultrafiltration membrane (YM10, produced by Amicon) having en exclusion molecular weight of 10,000, and the concentrated fraction was solvent-substituted with a 50 mM ammonium acetate buffer (pH 4.5). The fraction was adsorbed to an ion exchange chromatography column (diameter 2.6 cm, length 30 cm) using CM Sepharose CL6B (produced by Pharmacia) equilibrated with the same solvent. The column was washed with the initial solvent for 50 minutes, followed by elution with a linear concentration gradient (810 minutes) from a solution containing 15% to 50% of a 0.5M ammonium acetate buffer (pH 6.4) mixed in the initial solvent. An eluted fraction corresponding to an elution volume from 610 ml to 650 ml was fractionated and collected, followed by concentration by using the ultrafiltration membrane in the same manner as described above. After that, the solvent was substituted with a physiological saline solution containing 20 mM Tris-HCl (pH 7.4). A similar platelet aggregation-inhibiting activity was also present in an eluted fraction corresponding to an elution volume from 540 ml to 580 ml. Accordingly, this fraction was treated in the same manner as described above.

Figure 2:
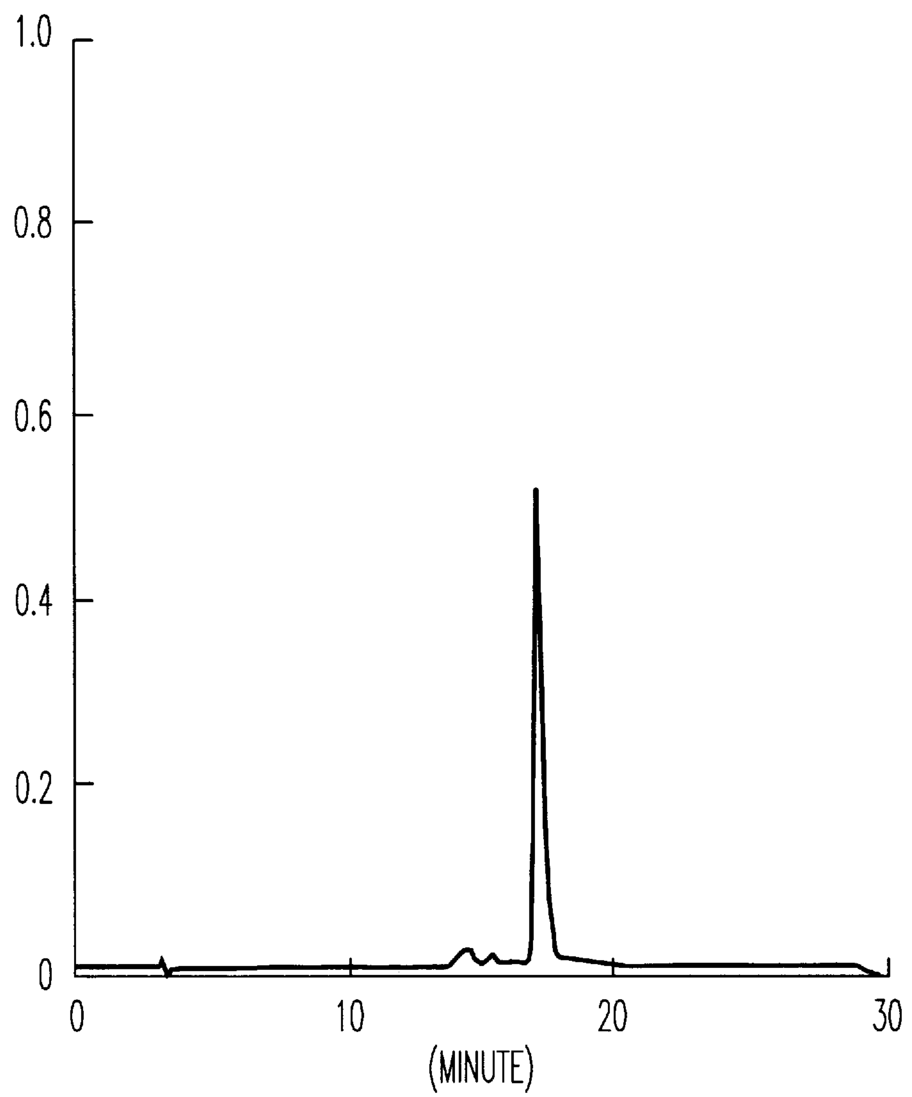
FIG. 2 shows a reverse phase chromatogram of CH-2.

Parts of the respective platelet aggregation-inhibiting activity fractions obtained by the ion exchange column chromatography were applied to high-performance liquid chromatography by using a reverse phase column (SSC-VP-304, produced by Senshu Kagaku, diameter: 4.6 mm, length: 250 mm). Analysis was performed by elution with a linear concentration gradient (20 minutes) from an acetonitrile concentration of 31% to a concentration of 52% containing 0.1% trifluoroacetic acid. As a result, the both fractions contained single peptides which were different with each other (FIGS. 1, 2). According to SDS-polyacrylamide gel electrophoresis, both of the peptides contained in the two active fractions presented one band having a molecular weight of about 25 kilodaltons under a non-reduced condition, and two bands having molecular weights of about 14 kilodaltons and 15 kilodaltons under a reduced condition obtained by adding 1% mercaptoethanol. It was found that the both are similar double strand peptides (SEQ ID NOS: 1 and 3). Accordingly, the peptide eluted in the latter active fractions from the ion exchange column (elution volume: 610 ml to 650 ml) was designated as CH-1, and the peptide eluted in the former active fractions (elution volume: 540 ml to 580 ml) was designated as CH-2.

Amino acid sequence analysis for an amino terminus of CH-1 was performed as follows. About 50 μg of CH-1 was dissolved in 100 μl of a 7M guanidine hydrochloride aqueous solution containing 0.5M Tris-HCl (pH 8.5) and 10 mM ethylenediaminetetraacetic acid disodium salt (EDTAsNa2) . After that, 4-vinylpyridine (1 μl) and tri-n-butylphosphine (2 μl) were added. A reaction was performed at room temperature overnight to carry out reducing pyridylethylation. The reaction solution was applied to high performance liquid chromatography by using a column of TSKgel-Phenyl-5PW-RP (produced by Tosoh Co., diameter: 4.6 mm, length: 75 mm) to separate each of produced peptide chains. Elution was performed at a flow rate of 1 ml/min with a linear concentration gradient (20 minutes) from an acetonitrile concentration of 31% to a concentration of 52% containing 0.1% trifluoroacetic acid. Each of the separated peptide chains was lyophilized, and then dissolved in 30% acetonitrile to perform amino acid sequence analysis from the amino terminus by using Protein Sequencer 470A (produced by Applied Biosystems). As a result, it was found that the amino acid sequences on the amino terminus of the respective chains were those shown in SEQ ID NO: 1 and 3 in Sequence Listing. They were respectively coincident with amino acid sequences on N-terminal sides of α-chain and β-chain of a peptide CHH—B isolated from the same snake venom as described in an international publication pamphlet of WO9208470. According to retention times of CH-2 and CH-1 in the analysis by using the reverse phase column chromatography shown in FIGS. 1 and 2, it was considered that CH-2 was similar to CHH-A, and CH-1 was similar to CHH-B described in the pamphlet.

<2> Activity of CH-1 upon Administration to Animal

The number of platelets was measured when CH-1 obtained as described above was administrated to guinea pigs. CH-1 was dissolved in a physiological saline solution to give concentrations of 10 to 100 μg/ml, and administrated intravenously to guinea pigs. After about 5 minutes, arterial blood was collected from abdominal aorta. Citric acid (0.32%) was used as a blood anticoagulant in the blood collection to measure the number of white blood corpuscles (WBC), the number of red blood corpuscles (RBC), and the number of platelets (PLT) by using Sysmex E-2000 (produced by Toa Medical Electronics).

Administration doses and the numbers of the respective corpuscles are shown in Table 1. Only the decrease in platelets was observed depending on the dose of administration. Almost complete disappearance of platelets was observed at an administration dose of 100 μg/kg or more.

TABLE 1

| Measurement item | Physiological saline | CH-1 (μg/kg) | | | | |
|---|---|---|---|---|---|---|
| | | 10 | 30 | 30 | 100 | 100 |
| WBC × $10^2$/μl | 35.0 | 18.0 | 20.0 | 19.0 | 19.0 | 21.0 |
| RBC × $10^4$/μl | 465.0 | 440.0 | 440.0 | 457.0 | 468.0 | 448.0 |
| PLT × $10^4$/μl | 38.3 | 41.0 | 9.6 | 13.7 | 0.4 | 0.8 |

<3> Trial to Convert Double Strand CH-1 into Single Strand (1) Reducing Carboxyamidomethylation for CH-1

Reducing carboxyamidomethylation for CH-1 was performed as follows. CH-1 (200 μg) was dissolved in 500 μl of a 7M guanidine hydrochloride aqueous solution containing 0.5M Tris-HCl (pH 8.5) and 10 mM ethylenediaminetetraacetic acid disodium salt (EDTA·Na2), to which 50 μl of a dithiothreitol aqueous solution (20 mg/ml) was added, followed by storage at 37° C. for 1 hour. An iodoacetoamide aqueous solution (50 μl, 50 mg/ml) was added to the stored solution to perform a reaction at room temperature for 30 minutes with shielding from light.

After the reaction, dialysis was performed at 4° C. overnight against a 0.15M sodium chloride aqueous solution (5 liters) containing 20 mM Tris-HCl (pH 7.4) by using a dialysis membrane Spectra/por1 (produced by Spectra, dialysis limit molecular weight: 6,000 to 8,000). Since white insoluble matters appeared after the dialysis, a surfactant of Tween-20 was added to give a final concentration of 2%. However, the insoluble matters were not dissolved. The white-turbid solution was concentrated by ultrafiltration by using Centricon-10 (produced by Amicon), and a suspension of 100 μl was finally obtained. The suspension was weakly centrifuged to obtain a supernatant. After that, an aliquot (10 μl) of the supernatant was used to investigate the inhibiting activity on ristocetin-mediated aggregation in accordance with the method described in the item <1>. However, the inhibiting activity was not found. It was considered that this result was obtained because CH-1 subjected to reducing carboxyamidomethylation by the method described above had no inhibiting activity on ristocetin-mediated aggregation, or because it consequently had an extremely low solubility in water.

(2) Reducing Pyridylethylation for CH-1

Reducing pyridylethylation for CH-1 was performed as follows. CH-1 (200 μg) was dissolved in 200 μl of a 7M guanidine hydrochloride aqueous solution containing 0.5M Tris-HCl (pH 8.5) and 10 mM ethylenediaminetetraacetic acid disodium salt (EDTA·Na2), to which 4-vinylpyridine (1 μl) and tri-n-butylphosphine (2 μl) were added to perform a reaction at room temperature overnight. The reaction solution was applied to high-performance liquid chromatography by using a reverse phase column (SSC-VP-304, produced by Senshu Kagaku, diameter: 4.6 mm, length: 250 mm). Elution was performed with a concentration gradient (20 minutes) from an acetonitrile concentration of 10% to a concentration of 59% containing 0.1% trifluoroacetic acid. Products were fractionated and collected as a mixture of two species of pyridylethylated peptides.

The fractionated fraction was lyophilized, and then the total amount was dissolved in 50 μl of a physiological saline solution containing 20 mM Tris-HCl (pH 7.4). An aliquot (10 μl) was used to observe the inhibiting activity on ristocetin-mediated aggregation in accordance with the method described in the item <1>. However, the inhibiting activity was not observed. It was considered that this result was obtained because CH-1 subjected to reducing pyridylethylation by the method described above had no inhibiting activity on ristocetin-mediated aggregation, or because it consequently had an extremely low solubility in water.

(3) Reduction of CH-1 with Mercaptoethanol and Reconstruction of Disulfide Bonds Operations were performed as follows for reduction of CH-1 with mercaptoethanol and reconstruction of disulfide bonds after the reduction with redox (oxidation-reduction) buffers by using reduced and oxidized glutathione.

CH-1 (240 μg) was dissolved in 120 μl of a 7M guanidine hydrochloride aqueous solution containing 0.5M Tris-HCl (pH 8.5) and 10 mM ethylenediaminetetraacetic acid disodium salt (EDTA·Na2), which was stored at 37° C. for 10 minutes. A 10% mercaptoethanol aqueous solution (1/9 volume) was added to the solution to give a final concentration of mercaptoethanol of 1%, followed by being stored to stand at 37° C. for 1 hour. After that, 2 ml of a solution (concentration of guanidine hydrochloride: 2M, hereinafter abbreviated as "2M guanidine hydrochloride preparation solution"), which was obtained by diluting the 7M guanidine hydrochloride aqueous solution containing 0.5M Tris-HCl (pH 8.5) and 10 mM ethylenediaminetetraacetic acid disodium salt (EDTA·Na2) by a factor of 2/7, was added, followed by ultrafiltration concentration by using Centricon-10 (produced by Amicon). The 2M guanidine hydrochloride preparation solution (2 ml) was added to the obtained concentrated solution, followed by ultrafiltration concentration again. This concentrating operation was repeated several times to remove mercaptoethanol. Thus a 2M guanidine hydrochloride preparation solution (380 μl) containing reduced products of CH-1 was obtained.

The solution containing reduced products of CH-1 was divided into 5 aliquots (each having a volume of 76 μl) to perform an operation for reconstructing disulfide bonds with redox buffers by using reduced and oxidized glutathione. The 2M guanidine hydrochloride preparation solution (374 μl) was added to each of the aliquots. Solutions (50 μl) obtained by mixing reduced and oxidized glutathione in ratios shown in Table 2 were further added respectively, followed by substitution with nitrogen. After that, the vessels were tightly sealed to perform the reaction at room temperature overnight.

TABLE 2

| Composition of redox buffer | Buffer 1 | 2 | 3 | 4 | 5 |
|---|---|---|---|---|---|
| Aqueous solution of 50 mM oxidized glutathione | 1 | 2 | 1 | 2 | 4 |
| Aqueous solution of 100 mM reduced glutathione | 5 | 5 | 1 | 1 | 1 |

(Numerical values indicate mixing ratios of the solutions.)

The five reaction solutions above and solutions immediately after reduction with mercaptoethanol were applied to high-performance liquid chromatography by using a reverse phase column (SSC-VP-304, produced by Senshu Kagaku, diameter: 4.6 mm, length: 250 mm). Analysis was performed by monitoring absorbance at 216 nm while performing elution by using a concentration gradient (20 minutes) from an acetonitrile concentration of 10% to a concentration of 59% containing 0.1% trifluoroacetic acid. However, no peak originating from any produced peptide was observed in all of the solutions.

It was considered that the result described above was obtained because CH-1 was converted into a reduced product having low solubility as a result of reduction with mercaptoethanol, and because the reduced product was not converted into a substance having high solubility by means of the oxidation-reduction reaction performed with the redox buffers.

(4) Reduction of CH-1 with Glutathione

A mild reducing reaction for CH-1 with glutathione was performed as follows. CH-1 (40 μg) was dissolved in the 2M guanidine hydrochloride preparation solution (450 μl) described above. After that, a solution (50 μl) of reduced glutathione (100 mM) dissolved in the same preparation solution was added, followed by being left to stand at 40° C. for 3 hours, and followed by being left to stand at room temperature for 5 days. The feature of products was analyzed by high-performance liquid chromatography by using a reverse phase column (SSC-VP318, produced by Senshu Kagaku, diameter: 4.6 mm, length: 250 mm). Elution was performed with a concentration gradient (20 minutes) from an acetonitrile concentration of 10% to a concentration of 80% containing 0.1% trifluoroacetic acid to observe absorbance at 216 nm.

Figure 3:
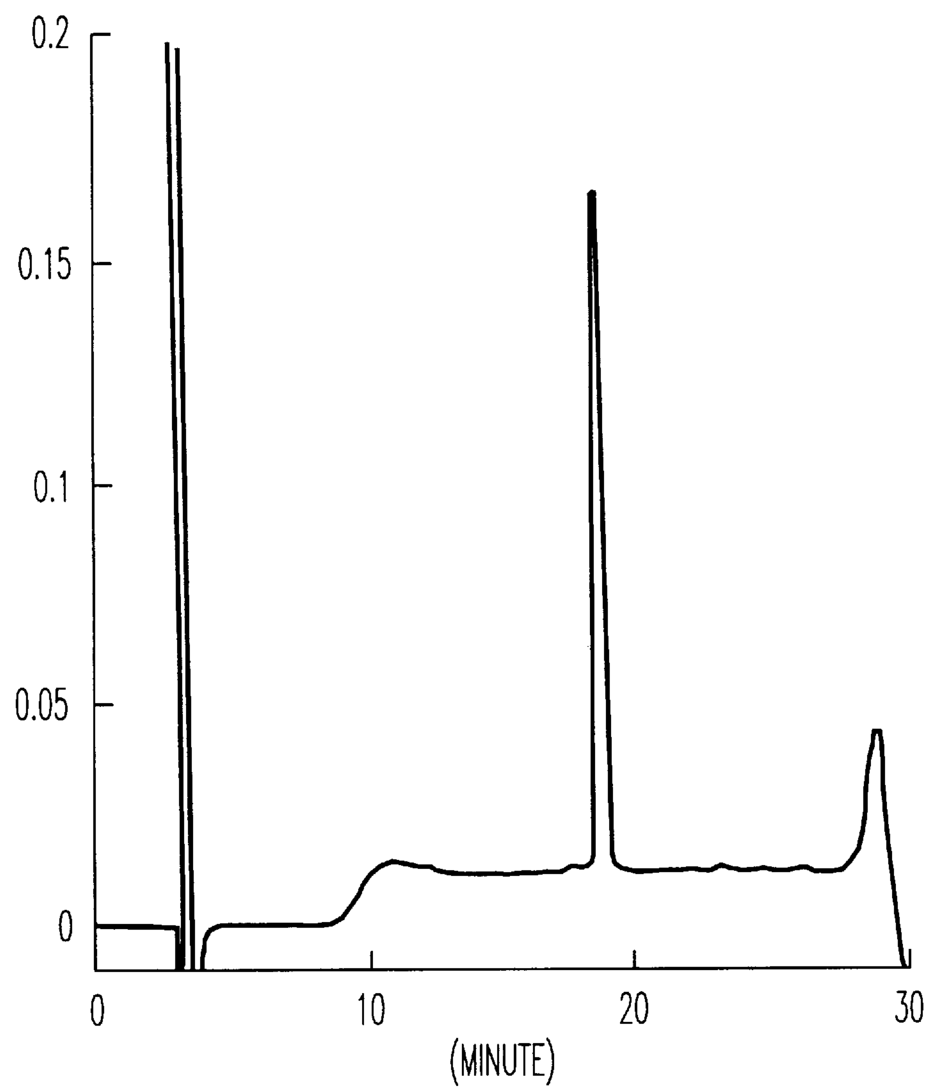
FIG. 3 shows a reverse phase chromatogram of CH-1 before addition of glutathione.
Figure 4:
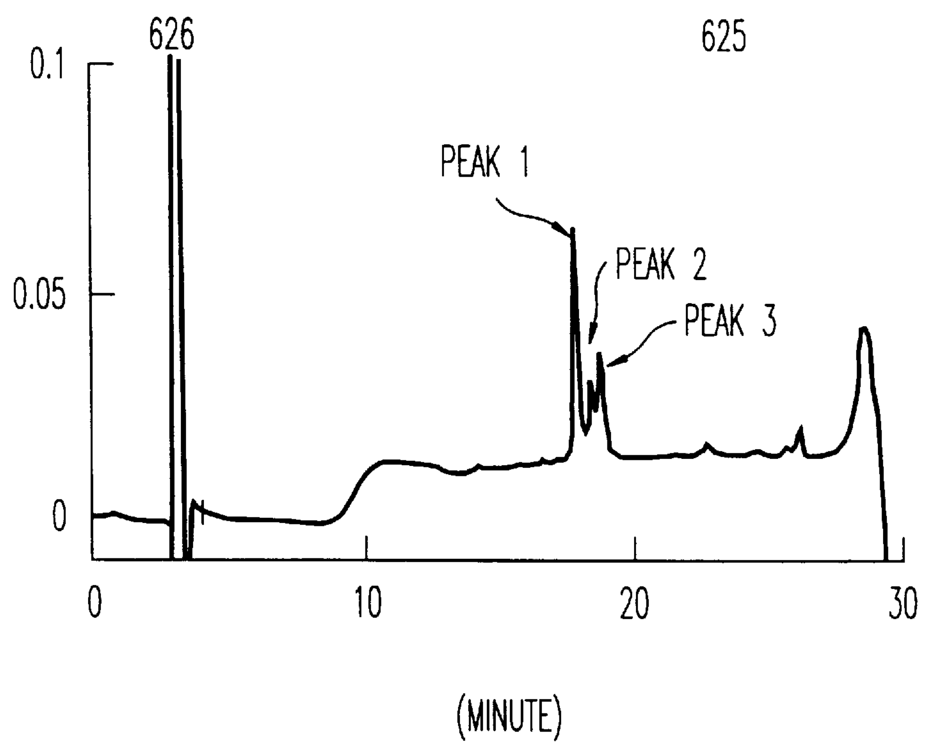
FIG. 4 shows a reverse phase chromatogram of substances produced from CH-1, 5 days after addition of glutathione.

FIGS. 3 and 4 show chromatograms before addition of glutathione (FIG. 3) and 5 days after addition of glutathione (FIG. 4). The total amount of the reaction solution after the reducing reaction with glutathione was separated by the same chromatography to fractionate and collect Peaks 1, 2, 3 shown in FIG. 4 respectively. Each of the peaks was lyophilized, and then the total amount was dissolved in a 0.15M sodium chloride aqueous solution (25 μl) containing 20 mM Tris-HCl (pH 7.4). An aliquot (10 μl) was used to measure the inhibiting activity on ristocetin-mediated aggregation in accordance with the method described in the item <1>. As a result, Peaks 1 and 3 had the inhibiting activity. However, Peak 3 was a peak of the raw material (CH-1). According to the result described above, it was revealed that the new substance (Peak 1) was generated by the method described above, the new substance having the inhibiting activity on ristocetin-mediated aggregation.

The effect of glutathione at various concentrations was investigated in the presence of 6M or 2M guanidine hydrochloride. CH-1 (36 μg) was dissolved in 234 μl of a solution (hereinafter referred to as "6M guanidine hydrochloride preparation solution") obtained by diluting a 7M guanidine hydrochloride aqueous solution containing 0.5M Tris-HCl (pH 8.5) and 10 mM ethylenediaminetetraacetic acid disodium salt (EDTA·Na2) by a factor of 6/7, or a solution (hereinafter referred to as "2M guanidine hydrochloride preparation solution") obtained by diluting the 7M guanidine hydrochloride aqueous solution by a factor of 2/7. To the solutions obtained by dissolving CH-1 in the 6M and 2M guanidine hydrochloride preparation solutions glutathion solutions (26 μl) having respective 10-fold concentrations were added so that the final concentration of reduced glutathione was 30 mM, 10 mM, 3 mM, and 1 mM respectively, and that the final concentration of oxidized glutathione was 30 mM. The feature of produced peaks after 1, 2, 3, 4, and 7 days was analyzed by high-performance liquid chromatography by using a reverse phase column (SSC-VP318, produced by Senshu Kagaku, diameter: 4.6 mm, length: 250 mm). Elution was performed with a concentration gradient (20 minutes) from an acetonitrile concentration of 24% to a concentration of 59% containing 0.1% trifluoroacetic acid monitoring absorbance at 216 nm.

Figure 5:
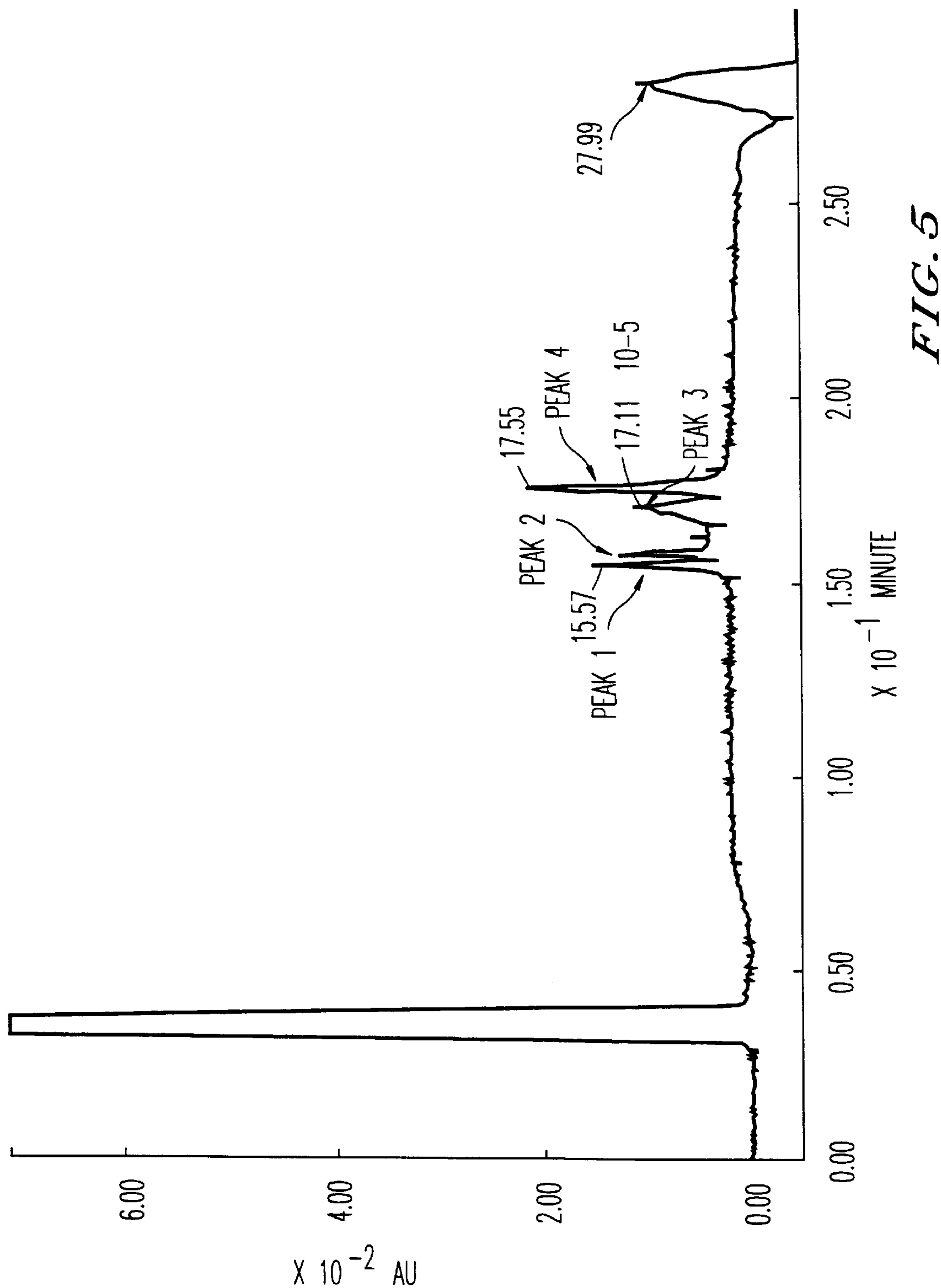
FIG. 5 shows a reverse phase chromatogram of substances produced from CH-1.
Figure 6A:
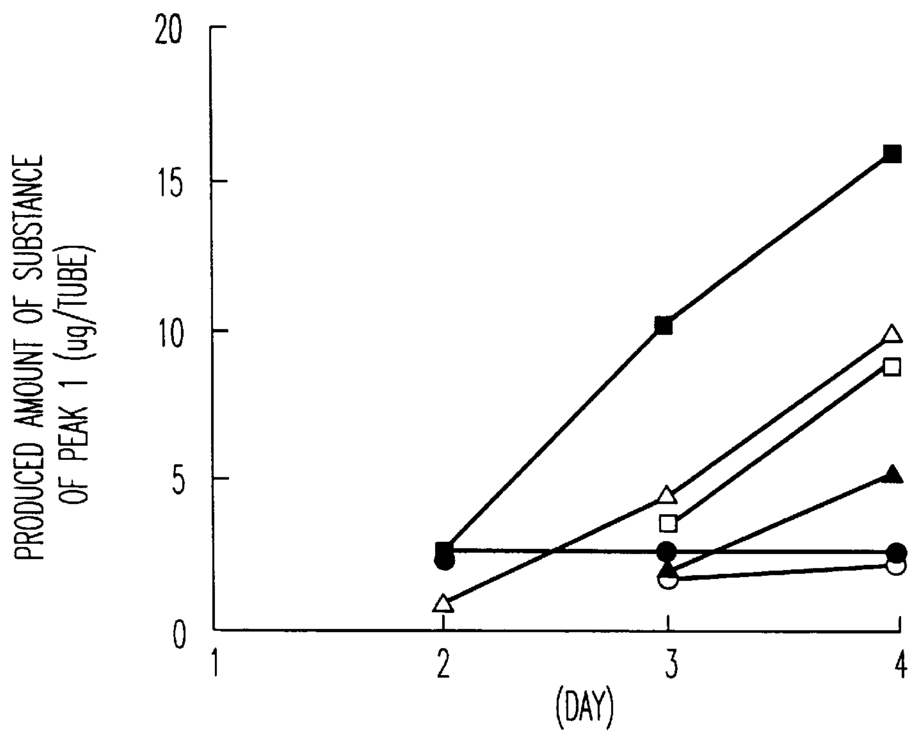
FIG. 6 shows production amounts (μg/tube) of (a) Peak 1 and (b) Peak 2 under respective conditions depending on the passage of time.
Figure 6B:
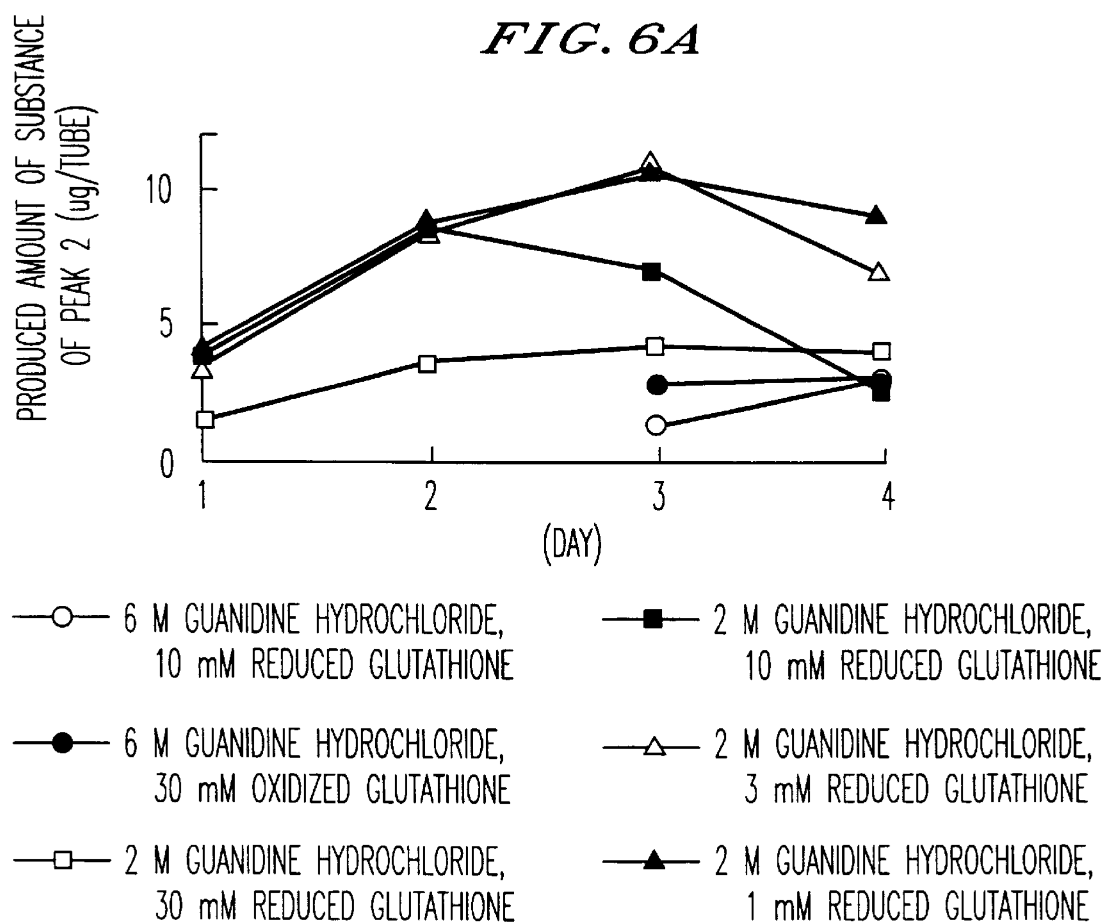

FIG. 5 shows one example of chromatogram obtained by this analysis (2M guanidine hydrochloride, 10 mM reduced glutathione, 4 days). Owing to this analysis system, it was found that those eluted at a retention time corresponding to Peak 1 shown in FIG. 4 contained two species of substances (corresponding to Peaks 1, 2 shown in FIG. 5). Peak 4 was a peak of the raw material (CH-1). Produced amounts of the substances contained in Peak 1 and Peak 2 changed depending on time under respective reaction conditions as shown in FIG. 6.

<4> Production of Single Strand Peptide from CH-1 by Using Reduced Glutathione

Distilled water (7.39 ml), a 7M guanidine hydrochloride aqueous solution containing 0.5M Tris-HCl (pH 8.5) and 10 mM ethylenediaminetetraacetic acid disodium salt (EDTA·Na2) (3.57 ml), and a 100 mM reduced glutathione (produced by Boehringer Mannheim) aqueous solution (1.25 ml) were added to a physiological saline aqueous solution of CH-1 (1.3 mg/ml, 290 μl), followed by storage at 28° C. for 5 days (final concentration of guanidine hydrochloride: 2M).

The solution after the storage was centrifuged at 3,000 rpm, and its supernatant was adjusted to be acidic (pH 4 or lower) by using trifluoroacetic acid. After that, the supernatant was applied to a reverse phase column (Vydac 214TP1022, produced by Vydac, diameter: 22 mm, length: 250 mm) at a flow rate of 15 ml/min to fractionate and collect produced peptides in accordance with elution by using a concentration gradient (20 minutes) from an acetonitrile concentration of 27% to a concentration of 45% containing 0.1% trifluoroacetic acid.

As a result, the same products as those shown in FIG. 5 were generated. Peak 1 and Peak 2 were designated as AS1051 and AS1052 respectively. As a result of SDS-polyacrylamide gel electrophoresis for each of them, it was demonstrated that AS1051 was a single-stranded peptide having a molecular weight of about 14 kilodaltons under a non-reduced condition and a molecular weight of about 15 kilodaltons under a reduced condition in the presence of 1% mercaptoethanol. It was also suggested that AS1052 was a homodimer comprising the same two peptides having molecular weights of about 26 and 15 kilodaltons under non-reduced and reduced conditions respectively.

The amino acid sequence and the manner of disulfide bonds of obtained AS1051 were determined as follows. A 1M Tris-HCl buffer (20 μl) containing 20 mM ethylenediaminetetraacetic acid disodium salt (EDTA), distilled water (120 μl), an aqueous solution (10 μl) containing 5 μg of lysylendopeptidase (produced by Wako Pure Chemical) were successively added to an aqueous solution (50 μl) containing 50 μg of AS1051 to perform an enzymatic digestion reaction at 37° C. for 2 hours. The reaction solution was applied to high-performance liquid chromatography by using a reverse phase column (SSC-VP-318, produced by Senshu Kagaku, diameter: 4.6 mm, length: 250 mm) to separate, fractionate and collect digested fragments. After that, each of the digested fragments was subjected to amino acid sequence analysis by using Protein Sequencer 470A (produced by Applied Biosystems). Thus the amino acid sequence of AS1051 was determined as shown in SEQ ID NO: 2 and FIG. 7. In this sequence, the number of amino acid residues was smaller by one, and 39th, 85th, and 86th amino acids were different, as compared with α-chain of CHH-B described in the international publication pamphlet of WO9208472.

Three Fragments A, B, C shown in FIG. 7 were obtained as one digested fragment bound through disulfide bonds. Accordingly, the fragment was further digested with proteinase Glu-C (produced by Boehringer Mannheim). As a result of amino acid sequence analysis for produced fragments, it was found that the disulfide bonds were formed between Cys4 and Cys15, between Cys32 and Cys120, and between Cys95 and Cys112. This bonding manner is common to C-type lectin including those originating from snake venom. Accordingly, it is considered that AS1051 maintains the manner of original disulfide bonds.

As a result of amino acid sequence analysis, it was found that double strand AS1052 was a homodimer comprising two chains of AS1051.

<5> Comparison of Platelet Aggregation-inhibiting Activities by Using Double Strand Peptide (CH-1) and Single-Sstranded Peptide (AS1051)

The inhibiting activity of the double strand CH-1 on platelet aggregation was compared with that of the single-stranded peptide AS1051. Fresh blood collected from healthy human added with a 1/10 volume of 3.8% sodium citrate was centrifuged at 900 rpm for 15 minutes to obtain human platelet rich plasma (PRP) to which these peptides were added to measure resulting platelet aggregation-inhibiting activities by using Hematracer-801 (produced by Niko Bioscience). The measurement was performed by adding 100 μl of the platelet rich plasma into a cuvette containing 12.5 μl of a peptide solution, agitating it at 37° C. for 3 minutes by using a stirrer bar, and then adding 12.5 μl of an agglutinogen to observe transmitted light.

Figure 8A:
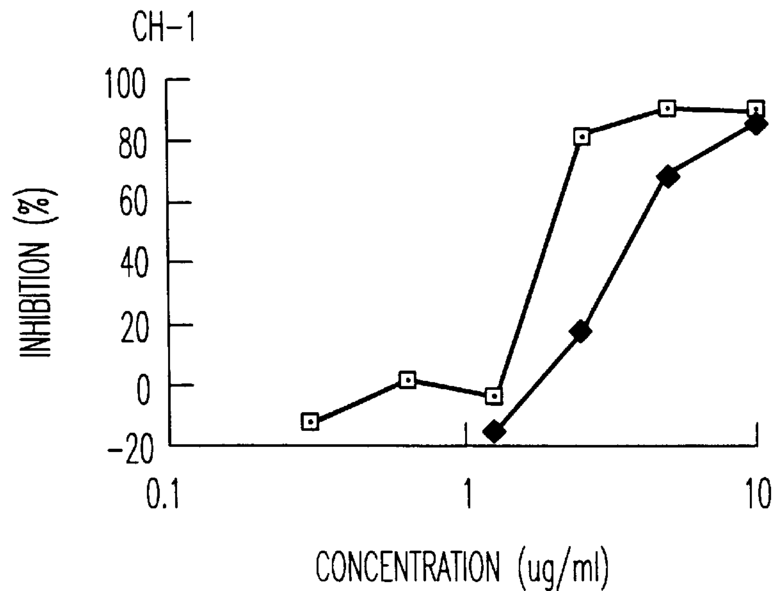
FIG. 8 shows inhibiting activities (inhibition ratio with respect to control) of (a) CH-1 and (b) AS1051 on ristocetin-mediated aggregation and botrocetin-mediated aggregation.
Figure 8B:
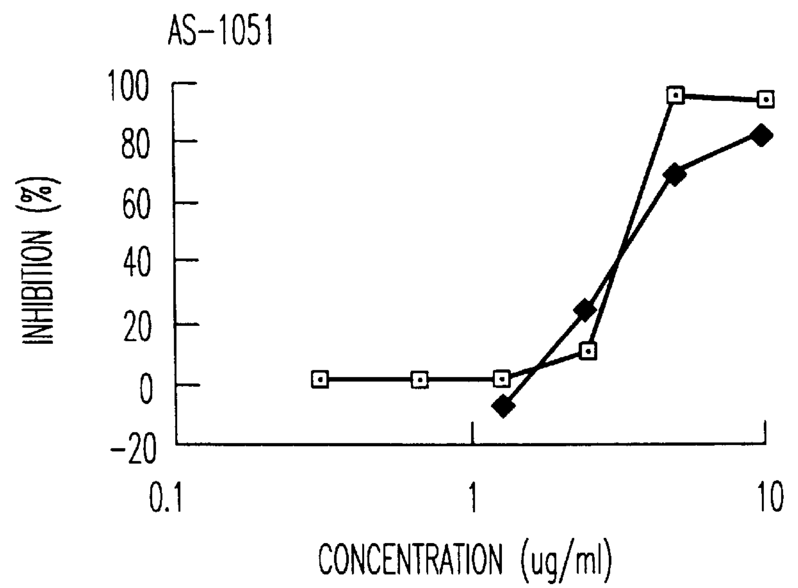

Ristocetin (final concentration: 1.2 mg/ml), botrocetin (1 μg/ml), ADP (3 μM), or collagen (10 μg/ml) was used as the agglutinogen to calculate the aggregation-inhibiting ratio with respect to a control group to which no peptide sample was added. FIG. 8 shows inhibiting activities of CH-1 and AS1051 on ristocetin-induced aggregation and botrocetin-induced aggregation. Almost the same inhibiting activity was observed for the both peptides (double strand peptide (CH-1), and single-stranded peptide (AS1051)) against ristocetin-induced aggregation and botrocetin-induced aggregation. The both peptides exhibited no inhibition on aggregation induced by ADP and collagen even at a concentration of 20 μg/ml, demonstrating that they specifically inhibited aggregation depending on the binding between von Willebrand factor and glycoprotein Ib, such as the ristocetin-induced aggregation and the botrocetin-induced aggregation.

It was also revealed that the double strand AS1052 had approximately the same inhibiting activity as that of AS1051.

<6> Comparison of Numbers of Platelets upon Administration of Double Strand Peptide (CH-1) and Single-stranded Peptide (AS1051) to Mice Physiological saline solutions of CH-1 and AS1051 (100 μg/kg for each), and only a physiological saline solution as a control were intravenously administrated to mice respectively. Blood was collected from hearts after 5 minutes to measure the number of white blood corpuscles (WBC), the number of red blood corpuscles (RBC), and the number of platelets (PLT) in the same manner as in the item <2>.

As shown in Table 3, platelets disappeared almost completely in the group of CH-1 administration (100 μg/kg). On the contrary, the decrease in platelets was not observed in the group of AS1051 administration (100 μg/kg). No change was observed in the number of white blood corpuscles (WBC) and the number of red blood corpuscles (RBC) both in the groups of CH-1 and AS1051 administration as compared with the control group. According to the fact described above, it was confirmed that the single-stranded AS1051 did not cause the decrease in platelets which was observed upon administration of the double strand peptide CH-1.

TABLE 3

| Measurement item | Physio-logical saline | AS1051 (100 μg/kg) | | | CH-1 (100 μg/kg) | | |
|---|---|---|---|---|---|---|---|
| WBC × $10^2/\mu l$ | 7.0 | 21.0 | 51.0 | 13.0 | 20.0 | 37.0 | 21.0 | 21.0 |
| RBC × $10^4/\mu l$ | 885.0 | 830.0 | 882.0 | 871.0 | 866.0 | 864.0 | 921.0 | 891.0 |
| PLT × $10^4/\mu l$ | 130.9 | 136.3 | 122.4 | 107.7 | 119.7 | 1.8 | 1.0 | 0.9 |

Figure 9:
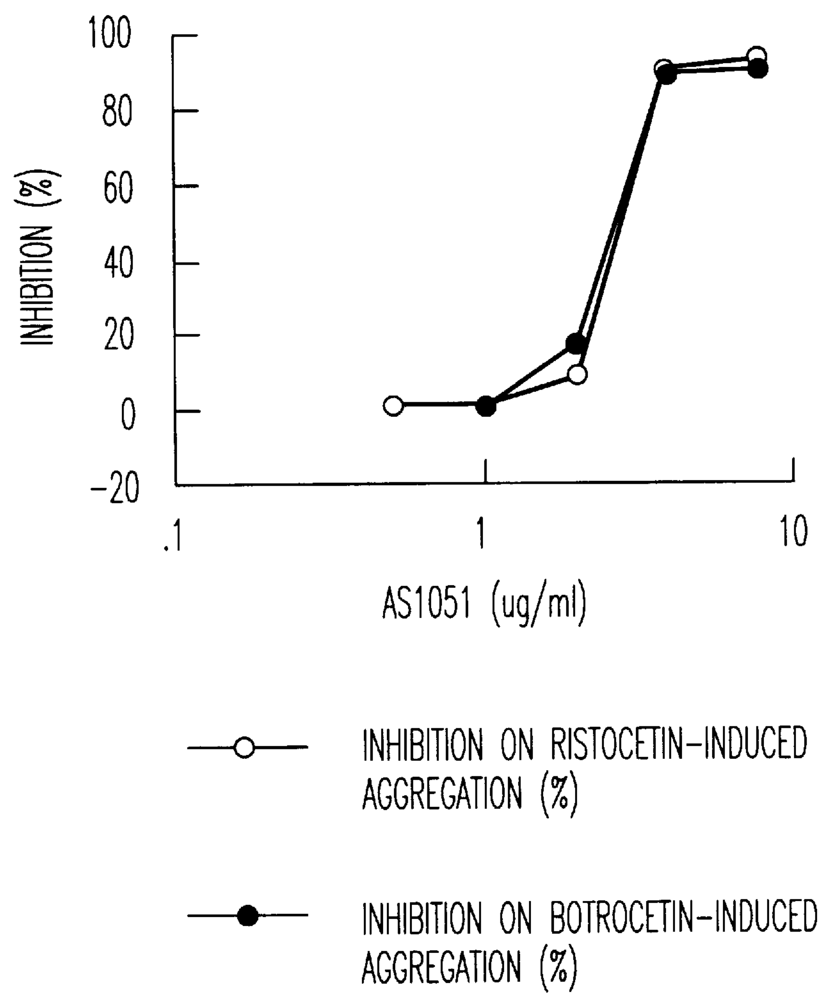
FIG. 9 shows inhibiting activities of AS1051 on ristocetin-mediated aggregation and botrocetin-mediated aggregation of guinea pig platelets.

<7> Measurement of Anti-thrombus Activity of Single-stranded Peptide by Using Guinea Pigs At first, the measurement was performed for inhibiting activities of the single-stranded peptide AS1051 on ristocetin-induced aggregation and botrocetin-induced aggregation of platelet rich plasma obtained from guinea pigs. As shown in FIG. 9, the inhibiting activities of AS1051 on the ristocetin-induced aggregation and the botrocetin-induced aggregation were at approximately the same degrees as those of the values obtained for the platelet rich plasma from human (FIG. 8).

Next, the numbers of corpuscles such as platelets were measured after administration of AS1051 to guinea pigs. Further, an exo-vivo test was performed by using platelet rich plasma prepared from blood collected after administration of AS1051 to measure whether or not the aggregation was inhibited. AS1051 (200 μg/kg) was intravenously administrated to guinea pigs. Arterial blood at 5 minutes after the administration was collected to measure the number of white blood corpuscles (WBC), the number of red blood corpuscles (RBC), and the number of platelets (PLT) (Table 4) in the same manner as in the item <2>.

TABLE 4

| Measurement item | Physiological saline | | | AS1051 (200 μg/kg) | | |
|---|---|---|---|---|---|---|
| WBC × $10^2/\mu l$ | 35.0 | 19.0 | 22.0 | 24.0 | 21.0 | 27.0 |
| RBC × $10^4/\mu l$ | 509.0 | 512.0 | 522.0 | 518.0 | 458.0 | 471.0 |
| PLT × $10^4/\mu l$ | 35.9 | 46.3 | 30.7 | 34.6 | 33.7 | 40.0 |

Figure 10A:
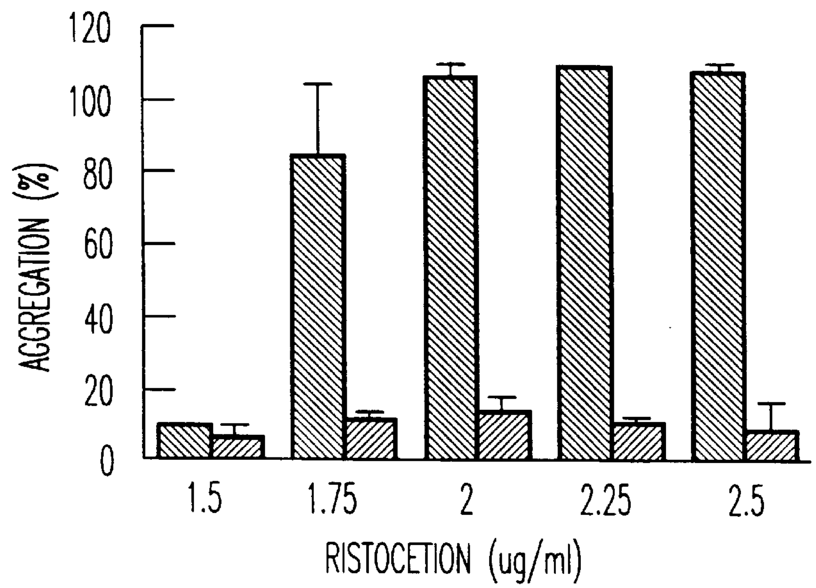
FIG. 10 shows aggregating activities of (a) ristocetin and (b) botrocetin on guinea pig platelets after administration of AS1051 (200 μg/kg).
Figure 10B:
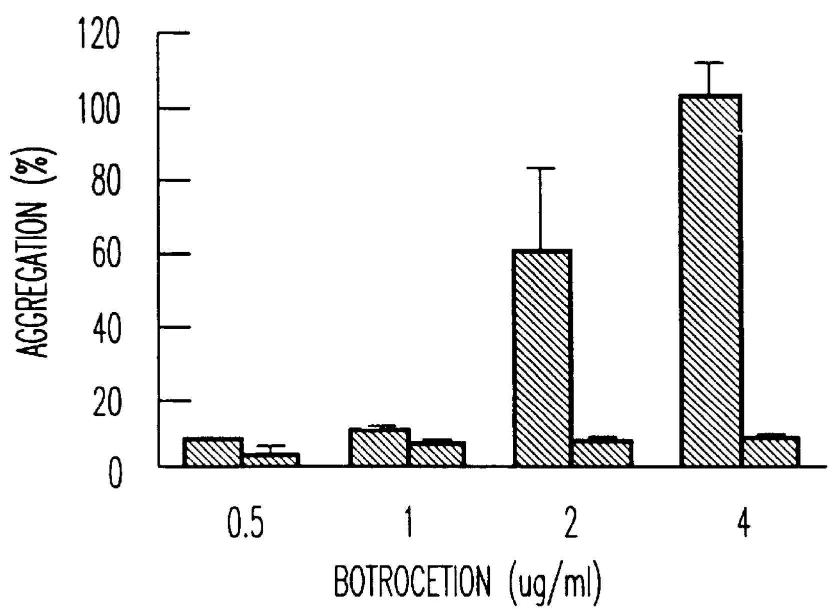

The same amount of bovine serum albumin (BSA) was added to the administrated preparations of AS1051, and those administrated with only BSA were used as a control group. No change was observed in the number of platelet, etc. in the AS1051-administrated group as compared with the control group. Platelet rich plasma was prepared from the blood to measure the features of ristocetin-induced aggregation and botrocetin-induced aggregation by using the same method as described above (FIG. 10). Observation was made by changing the amount of added ristocetin. It was demonstrated that the aggregation was almost completely inhibited in the AS1051-administrated group even at a ristocetin concentration at which the control group completely caused the aggregation. As for the botrocetin-induced aggregation, the same result was obtained.

According to the results described above, it was demonstrated that AS1051 did not affect the number of platelets upon intravenous administration to guinea pigs in an amount of 200 μg/kg in the same manner as in the item <5> described above (administration to mice), and that a sufficient concentration of AS1051 was maintained in blood to inhibit the ristocetin-induced aggregation and the botrocetin-induced aggregation.

Next, the anti-thrombus activity of AS1051 was evaluated in vivo by using an animal thrombosis model. An optically excited thrombus model reported by Matsuno et al. (Matsuno et al., *Blood and Circulation* (*Ketsueki-to-Jyunkan*), 4, pp. 20–23 (1990)) was used as the thrombosis model.

Figure 11:
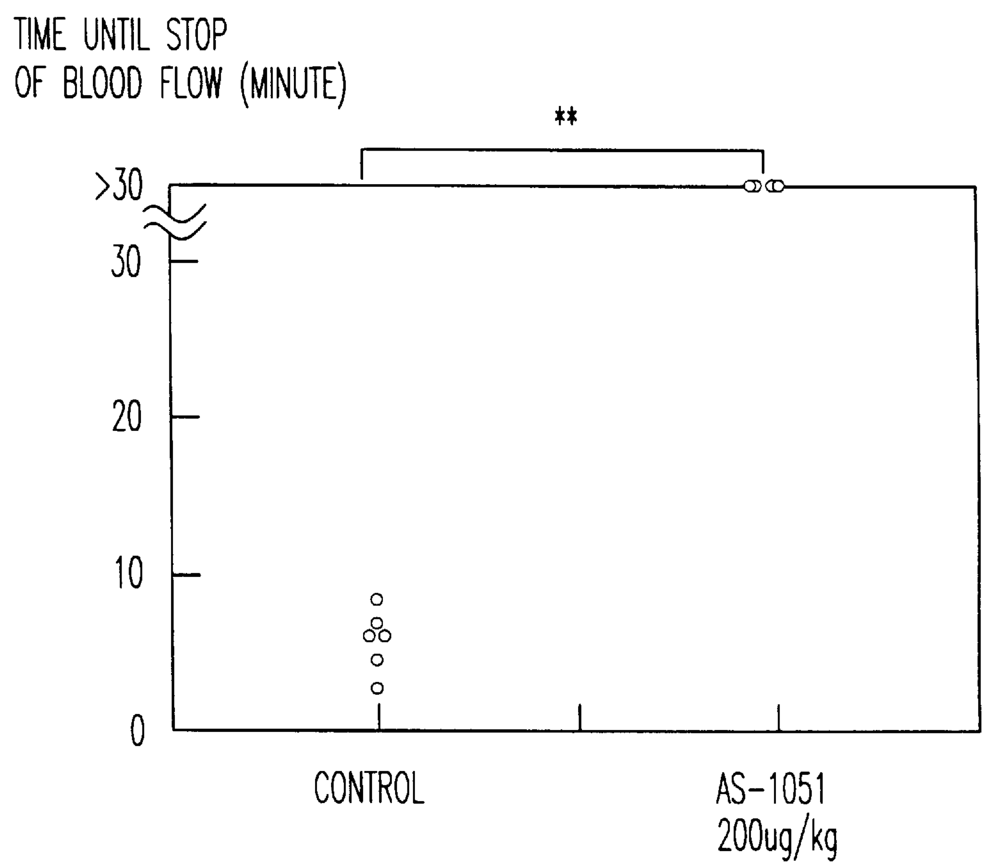
FIG. 11 shows an anti-thrombus activity of AS1051 (administration amount: 200 μg/kg) on optically excited thrombus model guinea pigs.

Carotid artery of each of guinea pigs was exfoliated to install a Doppler blood flow probe. A xenon lamp light source was provided at a position spaced by a distance of about 5 mm upstream from the blood vessel installed with the probe. A sample of AS1051 containing BSA (the amount of BSA was the same as the amount of AS1051) or a sample containing only BSA as a control was intravenously administrated to guinea pigs. After 5 minutes, a rose bengal solution (10 mg/kg) was intravenously administrated. Simultaneously, a light beam of 540 nm was radiated to damage blood vessel walls. Thus the time until stop of blood flow was measured by using a pulse Doppler blood flow meter. As shown in FIG. 11, the time until stop of blood flow was clearly prolonged in the AS1051-administrated group (200 μg/kg) as compared with the control group, demonstrating that AS1051 had the anti-thrombus activity ($p<0.01$).

EXAMPLE 2

Production of Anti-Thrombus Single Strand Peptide by *Escherichia coli*

In order to produce the peptide of the present invention by using genetic engineering techniques, a gene coding for the peptide having the activity to inhibit the binding of von Willebrand factor with platelets was isolated from *Crotalus horridus horridus*, and it was expressed in *Escherichia coli.*

<1> Preparation of cDNA Library of *Crotalus horridus horridus*

(1) Extraction of mRNA from *Crotalus horridus horridus*

A venom gland of *Crotalus horridus horridus* was excised. It was immediately frozen with liquid nitrogen, and stored until use. The poison gland (1.7 g) was disrupted with Polytron Homogenizer (produced by Kinematica) in 20 ml of an RNA-extracting solution (4M guanidium isothiocyanate hydrochloride, 0.1M Tris-HCl (pH 7.5), 1% β-mercaptoethanol, 0.1% lauryl sarcosyl sodium salt). The disrupted suspension was centrifuged at 10,000×G for 10 minutes to remove insoluble matters. After that, a supernatant was overlaid on an equal amount of a density-equilibrating buffer (4M cesium chloride, 10 mM ethylenediaminetetraacetic acid disodium salt pH 7.5) in a ultracentrifugation tube, and it was centrifuged at 30,000 rpm at 20° C. for 18 hours to separate 600 μg of total RNA.

mRNA was prepared from the total RNA by using a POLY(A) QUICK mRNA extraction kit (produced by Stratagene) in accordance with a protocol of the kit. Namely, a part of the obtained total RNA (500 μg) was adsorbed to an oligo dT column. The column was washed twice with a higher salt buffer (200 μl) and three times with a lower salt buffer (200 μl). After that, an elution buffer (200 μl) was allowed to pass through the column four times at 65° C. to separate and purify mRNA (10 μg).

(2) Synthesis of cDNA cDNA was synthesized by using a Time Savor DNA synthesis kit (produced by Pharmacia) in accordance with a protocol of the kit. Namely, the purified mRNA (3 μg) was mixed with a first strand reaction solution containing random hexamer primers (0.3 μg), 1 mM dithiothreitol, and reverse transcriptase, followed by a reaction at 37° C. for 1 hour to synthesize a first strand.

The reaction solution was mixed with a second strand reaction solution containing *Escherichia coli* RNase H and *Escherichia coli* DNA polymerase, followed by reactions at 12° C. for 30 minutes and at 22° C. for 1 hour to synthesize cDNA. Incubation was further performed at 65° C. for 10 minutes. After that, the reaction solution was treated with phenol/chloroform to inactivate the enzyme activity. Next, a gel filtration span column attached to the kit was used to perform centrifugation at 400×G for 2 minutes. Thus unreacted primers were removed to obtain double strand cDNA (3 μg).

(3) Preparation of cDNA Library

An EcoRI/NotI adapter attached to the Time Savor DNA kit was ligated to both ends of the double strand cDNA obtained as described above in accordance with a protocol of the kit. Namely, cDNA (3 μg), the EcoRI/NotI adapter (3 μl), a polyethylene glycol buffer (30 μl), an ATP solution (1 μl), and T4 DNA ligase (1 μl) were mixed to perform a ligation reaction at 16° C. for 1 hour. The reaction solution was further incubated at 65° C. for 10 minutes to inactivate the enzyme activity. After that, an ATP solution (1.5 μl) and T4 polynucleotide kinase (1 μl) were added, and reacted at 37° C. for 30 minutes to phosphatize the 5'-end of the adapter. After that, the reaction solution was incubated at 65° C. for 10 minutes, and treated with phenol/chloroform to inactivate the enzyme activity. Next, a gel filtration span column attached to the kit was used to centrifuge the reaction solution at 400×G for 2 minutes. Thus unreacted adapter was removed.

cDNA with the ligated adapters at both ends was ligated with an EcoRI site of a lambda phage vector λZAPII (produced by Stratagene) to prepare recombinant phage DNA. Namely, λZAPII/EcoRI/CIAP arm (1 μg) and a ligation buffer (100 mM Tris-HCl (pH 7.6), 25 mM magnesium chloride, 300 mM sodium chloride) were added to 400 ng of cDNA with the ligated adapters, to which an enzyme solution (B solution, produced by Takara Shuzo, Ligation Kit) containing T4 DNA ligase was added in an equal amount to perform a ligation reaction at 26° C. for 10 minutes.

Recombinant phage DNA obtained as described above was packaged by using a packaging kit GIGAPACKII GOLD (produced by Stratagene) in accordance with a protocol of the kit. Namely, λZAPII arm DNA (3 μg) ligated with cDNA described above was mixed with a packaging extraction solution of the kit to execute packaging by performing a reaction at 22° C. for 2 hours. This reaction solution was added with 500 μl of a phage dilution solution (0.58% sodium chloride, 0.2% magnesium sulfate, 50 mM Tris-HCl (pH 7.5), 0.01% gelatin).

The titer of the obtained recombinant phage was checked. After that, a phage library was prepared by using a half amount of the phage packaging reaction solution, and using *Escherichia coli* XL-1 Blue (produced by Stratagene) as a recipient. Namely, 10 plates each having a diameter of 150 mm containing a plaque formation medium (Bactotryptone 1%, yeast extract 0.5%, sodium chloride 0.5%, magnesium sulfate 1 mM, maltose 0.2%) were prepared. The phage diluted with the phage dilution solution, and the recipient were plated on the 10 plates so that 20,000 plaques would be formed per one plate, followed by cultivation at 37° C. for 12 hours to obtain the library of the recombinant phage.

<2> Preparation of Probe DNA for Isolating Objective Gene (1) Amplification of Partial Fragment of Objective Gene by RT-PCR Method The total RNA from *Crotalus horridus horridus* was used as a material to amplify DNA coding for the peptide capable of inhibiting the binding of von Willebrand factor with platelets in accordance with the RT-PCR method.

Based on the amino acid sequence of the peptide shown in SEQ ID NO: 2, its sections with less degeneracy of codons were selected to prepare primers for RT-PCR (reverse transcription polymerase chain reaction). Primers were chemically synthesized by an entrusted company, Biologica. SEQ ID NOS: 4 and 5 show nucleotide sequences of these primers. However, in SEQ ID NO: 4, 3rd and 6th nucleotides are mixtures of A and G, and 12th nucleotide is a mixture of T, C, A, and G. In SEQ ID NO: 5, 3rd nucleotide is a mixture of T, C, A, and G, 6th and 15th nucleotides are mixtures of T and C, and 9th nucleotide is a mixture of A and G.

RT-PCR was performed by using the primer described above for the total RNA of *Crotalus horridus horridus* prepared in the same manner as described above. In order to synthesize a first strand, the total RNA (5 μg) was mixed with reverse transcriptase SUPERSCRIPT II (produced by GIBCO) (2.5 μl), a first strand buffer (20 μl) attached to the enzyme solution, 0.1M dithiothreitol (10 μl), and 10 mM dNTP (5 μl). A reaction was performed at 42° C. for 1 hour to synthesize the first strand. The reaction solution was incubated at 95° C. for 5 minutes to inactivate the reverse transcriptase. Next, the first strand was used as a template to perform the PCR process. Namely, the first strand reaction solution (5 μl), a PCR reaction buffer (10 μl), 10 mM dNTP (5 μl), the primers (each 800 pmol), Taq polymerase (10μ) were mixed to perform a reaction over 25 cycles by using DNA Thermal Cycler (produced by Perkin-Elmer), one cycle comprising periods at 95° C. for 0.5 minute, at 52° C. for 1 minute, and at 72° C. for 2 minutes.

The PCR reaction solution was subjected to 2% agarose gel electrophoresis to analyze amplified DNA. As a result, a band of DNA was observed at a position of about 300 base pairs.

(2) Determination of Nucleotide Sequence of Amplified Fragment

The DNA fragment amplified as described above was subcloned into a plasmid by using a pCR-ScriptSK(+) cloning kit (produced by Stratagene) in accordance with a protocol of the kit. Namely, the PCR reaction solution was added and mixed with a ligation buffer, 1 mM ATP, pCR-script (produced by Stratagene) as a vector (10 ng), restriction enzyme SrfI (5 units), and T4 DNA ligase to perform a ligation reaction at 25° C. for 1 hour. After that, the reaction solution was incubated at 65° C. for 10 minutes to inactivate ligase. This reaction product was used to transform *E. coli* DH5α by the competent cell method, followed by plating on an L-Ap plate (Bactotryptone 1%, yeast extract 0.5%, sodium chloride 0.5%, sodium ampicillin 100 μg/ml) to perform cultivation at 37° C. for 18 hours. Bacterial cells which formed colonies were separated from the plate, a part of which was cultivated in a liquid medium to prepare a plasmid in accordance with the alkaline method ("Molecular Cloning", 2nd edition, Vol. 1, published by Cold Spring Harbor Press). This plasmid was designated as pCHAprobe.

The nucleotide sequence of the cloned fragment of pCHAprobe was analyzed by the dye Terminator method by using M13M4 or M13 reverse (produced by Takara Shuzo) as a primer, and using DNA Sequencer A373 (produced by Applied Biosystems) in accordance with the method of use of the sequencer. As a result, the cloned DNA fragment comprised 272 base pairs, and had a nucleotide sequence shown in SEQ ID NO: 6. When the sequence was translated into amino acids, the amino acids corresponded to those of a part of the objective peptide. Thus it was possible to demonstrate that the obtained cloned fragment was a part of the objective gene of the peptide AS1051.

(3) Labeling of Probe pCHAprobe was digested with restriction enzymes SacI and BamHI at corresponding sites existing at both ends of the cloned insert fragment. A DNA fragment having a size of 340 base pairs was separated by 2% agarose gel electrophoresis. DNA was recovered by using a DNA recovery kit (Takara EASYTRAP, produced by Takara Shuzo) in accordance with a protocol of the kit. This DNA (25 ng) was labeled with radioisotope by using [α-$^{32}$P]dCTP and a random primer labeling kit (produced by Takara Shuzo). Unreacted [α-$^{32}$P]dCTP was removed from the labeling reaction solution by using Nick column for gel filtration (produced by Pharmacia) to obtain a labeled probe.

<3> Preparation of Objective Gene by Plaque Hybridization

A gene coding for an entire length of the AS1051 peptide was screened from the cDNA phage library in accordance with plaque hybridization by using the probe described above.

Plaques of the λZAPII cDNA phage library were formed on a plate as described above. The plaques were transferred from the plate to a nylon filter Highbond-N (produced by Amersham) in accordance with a recipe attached to the filter. The filter is alkaline-treated to achieve lysis of phage. After that, phage DNA was immobilized to the filter by baking at 80° C. for 2 hours.

The filter was hybridized with the $^{32}$P-labeled probe (1×10$^{6}$ cpm/ml) at 37° C. for 16 hours in a solution containing 5×SSPE buffer (20×SSPC: 3.6M sodium chloride, 0.2M sodium phosphate buffer pH 7.7, 20 mM EDTA disodium salt), 30% formamide, 5×Denhardt's solution (100×Denhardt's solution: 2% bovine serum albumin, 2% Ficoll 400, 2% polyvinyl pyrrolidone), and 0.5% SDS. After that, the filter was washed twice at room temperature in 6×SSC (20×SSC: 3M sodium chloride, 0.3M trisodium citrate) and 0.1% SDS, and further it was washed twice at 50° C. in 2×SSC and 0.1% SDS to remove the probe non-specifically bound with the filter. An X-ray film HP20 (produced by Fuji Photo Film) was exposed with the filter at −80° C. for 24 hours. Clones corresponding to positive spots on the film were isolated from the phage plate to provide positive clones in primary screening. Similar screening operation was repeated to obtain positive clones which formed single plaques.

The λZAPII cDNA phages of the obtained positive clones were infected with a helper phage ExAssist (produced by Stratagene). SOLR cells (produced by Stratagene) provided as non-amber suppressor *Escherichia coli* were infected therewith. Thus strains of *Escherichia coli* were obtained, which harbored plasmids containing the cDNA fragment inserted into an EcoRI site of a plasmid pBluescriptSK(−) (produced by Stratagene). The plasmids were prepared from cells of these strains in accordance with the alkaline SDS method. The nucleotide sequence of the inserted fragment was determined by using DNA Sequencer A373 (produced by Applied Biosystems).

As a result, four positive clones had nucleotide sequences coding for the objective peptide. The harbored plasmids were designated as pCHA1, pCHA2, pCHA3, and pCHA4 respectively. *E. coli* harboring pCHA1 (HB101/pCHA, *E. coli* AJ13023) has been internationally deposited under a deposition number of FERM BP-4781 based on the Budapest Treaty since Aug. 12, 1994 in National Institute of Bioscience and Human Technology of Agency of Industrial Science and Technology of Ministry of International Trade and Industry (postal code: 305, 1–3 Higashi-Icchome, Tsukuba-shi, Ibaraki-ken, Japan). SEQ ID NO: 7 in Sequence Listing shows a nucleotide sequence of the gene coding for the AS1051 peptide cloned as described above. SEQ ID NO: 8 shows an amino acid sequence of the peptide encoded by the gene. This gene had a typical secretion signal comprising 22 amino acids including methionine as an amino acid for initiation of translation and following amino acids.

<4> Expression and Production of AS1051 Peptide by Using *Escherichia coli* as Host and Preparation of Active Peptide (1) Construction of *Escherichia coli* Expression Plasmid pCHAT7

Figure 12:
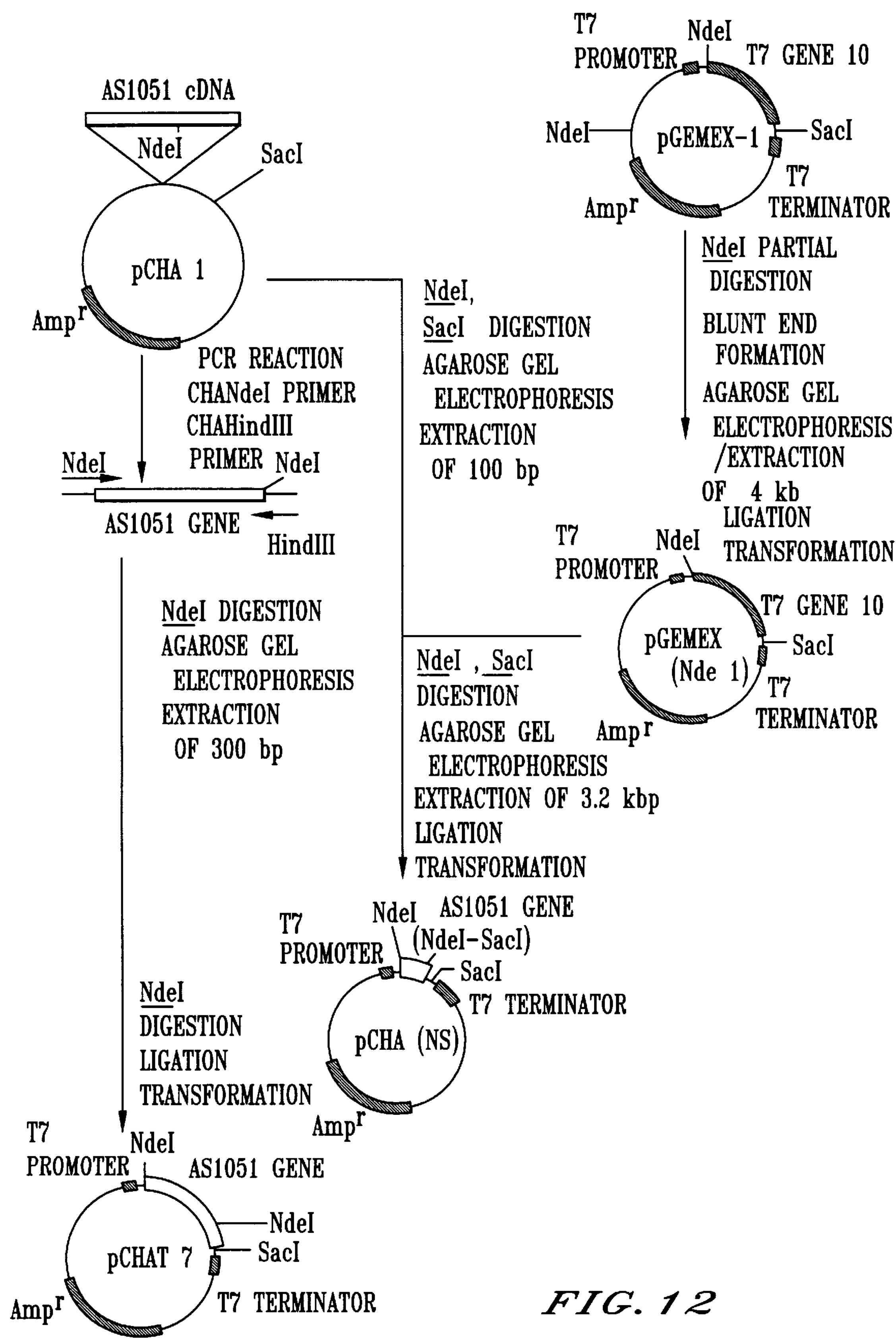
FIG. 12 shows construction steps for an AS1051 expression plasmid pCAHT7 for *Escherichia coli.*

The DNA fragment coding for the AS1051 peptide obtained as described above was introduced into a plasmid pGEMEX-1 (produced by Promega) containing T7 promoter to construct an expression plasmid for *Escherichia coli* (see FIG. 12).

At first, in order to facilitate the following operations, an NdeI cleavage site far from the T7 promoter was selected from two restriction enzyme NdeI cleavage sites existing in pGEMEX-1, and it was delected to prepare a plasmid. Namely, pGEMEX-1 was partially digested with NdeI. Digested ends were blunt-ended by using DNA Blunting Kit (produced by Takara Shuzo). Circular plasmids were formed again by using Ligation Kit (produced by Takara Shuzo). Obtained plasmids were used to transform *Escherichia coli*. A plasmid having only one NdeI cleavage site existing at the objective position was obtained from transformants, which was designated as pGEMEX(NdeI).

pCHA1 described above and pGEMEX(Nde1) were digested with restriction enzymes NdeI and SacI to extract DNA fragments of 100 base pairs and 3.2 kilo base pairs respectively by agarose gel electrophoresis. The DNA fragment of 100 base pairs originating from pCHA1 contained a 3'-end region (corresponding to nucleotide numbers 490 to 559 in SEQ ID NO: 7) of the gene coding for the AS1051 peptide.

A ligation reaction for these DNA fragment was performed by using Ligation Kit (produced by Takara Shuzo). The reaction solution was used to transform *Escherichia coli* HB101. A recombinant plasmid pCHA(NS) was obtained from transformants separated on an ampicillin-containing plate.

Next, a 5'-end region (corresponding to nucleotide numbers 135 to 489 in SEQ ID NO: 7) of the gene coding for the AS1051 peptide was inserted into the obtained plasmid pCHA(NS) to construct a plasmid for expressing and producing the AS1051 peptide in *Escherichia coli.*

In order to incorporate the 5'-end region of the gene coding for the AS1051 peptide into pCHA(NS), DNA primers were synthesized for amplifying the region in accordance with the PCR method. In this procedure, as for the primer for the 5'-end Bide, a primer containing an NdeI recognition sequence (CHANdeI primer: SEQ ID NO: 9) was used so that the 5'-end of an amplified fragment had an NdeI site. This primer also had a nucleotide sequence ATG as a translation initiation signal (nucleotide numbers 9 to 11 in SEQ ID NO: 9) before a codon of aspartic acid as the N-terminal amino acid of the AS1051 peptide on the 5'-end side. It is noted that the initiation codon overlaps the NdeI recognition sequence (nucleotide numbers 6 to 11 in SEQ ID NO: 9).

As for the primer for the 3'-end side, a primer containing a HindIII recognition sequence (CHAHindIII: SEQ ID NO: 10, the HindIII recognition sequence corresponds to nucleotide numbers 10 to 15) was used considering the construction of an expression plasmid to be used for an expression system for cultured insect cells described below.

The gene coding for the AS1051 peptide was amplified in accordance with the PCR process by using the primers described above. The PCR process was repeated over 25 cycles, one cycle comprising periods at 94° C. for 15 seconds, at 50° C. for 1 minute, and at 72 ° C. for 2 minutes. The PCR reaction solution was treated with phenol/chloroform to inactivate Taq polymerase. The amplified DNA fragment comprising 400 base pairs was purified in accordance with the ethanol precipitation method, and then it was digested with the restriction enzyme NdeI. This DNA fragment was ligated with pCHA(NS) having been digested with the restriction enzyme NdeI by using Ligation Kit (produced by Takara Shuzo). An obtained plasmid was used to transform *E. coli* HB101 strain in accordance with the competent cell method. A transformant was cultivated for 16 hours on an ampicillin-containing plate.

A plasmid was prepared from the grown transformant in accordance with the alkaline SDS method. The nucleotide sequence was determined by using T7 primer and SP6 primer (produced by Stratagene) and using DNA Sequencer A373 (produced by Applied Biosystems). Thus it was confirmed that the objective AS1051 peptide expression vector was constructed. The constructed expression vector was designated as pCHAT7. The plasmid construction process described above is shown in FIG. 12.

(2) Production of Peptide by *Escherichia coli*

In order to produce the AS1051 peptide by *Escherichia coli* by using the AS1051 peptide expression vector pCHAT7, *E. coli* JM109(DE3) (produced by Promega) was transformed with pCHAT7 in accordance with the competent cell method, which was cultivated at 25° C. for 2 days on an ampicillin-containing plate to select a plasmid-harboring strain. It is noted that *E. coli* JM109(DE3) is a strain having an RNA polymerase gene of T7 phage connected downstream from lacUV5 promoter, which is constructed to efficiently express only T7 promoter such that transcription by lacUV5 promoter is induced upon addition of IPTG (isopropyl-β-D-thiogalactopyranoside) to produce RNA polymerase of T7 phage. Therefore, the plasmid-harboring strain efficiently expressesd the AS1051 peptide.

*E. coli* JM109(DE3)/pCHAT7 harboring the expression plasmid was inoculated to 10 Sakaguchi flasks each having a volume of 500 ml containing 100 ml of an LB-Ap medium (1% Bactotryptone, 0.5% yeast extract, 0.5% sodium chloride, 100 μg/ml ampicillin), and cultivated at 30° C. for 16 hours with shaking. The inducing agent IPTG was added to the medium to give a final concentration of 0.5 mM to further continue cultivation at 37° C. for 4 hours with shaking. After the cultivation, bacterial cells were collected by centrifugation, and then suspended in 100 ml of a buffer (30 mM Tris-HCl pH 7.5, 10 mM EDTA (ethylenediaminetetraacetic acid disodium salt), 30 mM sodium chloride) to wash the bacterial cells. The cells were collected again by centrifugation, and suspended in 20 ml of a cell disruption buffer (0.5M EDTA, pH 8). Egg white lysozyme (20 mg) was added to this suspension to treat it at 0° C. for 1 hour to disrupt cell walls of the cells. The suspension was further disrupted and treated with a ultrasonic disrupter Insonator 200M (produced by Kubota) at 180 W for 10 minutes. An insoluble fraction of the cells (inclusion bodies) was obtained by centrifuging the disrupted suspension at 6,000 rpm for 20 minutes.

(3) Solubilization and Activation of Inclusion Bodies

Inclusion bodies obtained from 1 liter of culture liquid were dissolved in 7M guanidine hydrochloride solution (28.6 ml) containing 10 mM EDTA and 0.5M Tris-HCl (pH 8.5), to which 71.4 ml of distilled water was added, followed by storage at 4° C. for 2 days to perform oxidation with air. After that, this solution was made acidic by adding 0.5 ml of trifluoroacetic acid, and then insoluble matters were removed by centrifugation. A supernatant was fractionated and collected by high-performance liquid chromatography (HPLC) by using a reverse phase column (Vydac 214TP1022, produced by Vydac) to obtain recombinant AS1051 (9.0 mg). The obtained purified peptide provided the same molecular weight as that of AS1051 described in Example 1 <4> on SDS-polyacrylamide gel electrophoresis. The inhibiting activity on platelet aggregation approximately was measured for the obtained recombinant AS1051 by using the same method as described in Example 1<5>. As a result, the ADP-induced aggregation and the collagen-induced aggregation were not inhibited, while equivalent inhibiting activities were exhibited on the ristocetin-induced aggregation and the botrocetin-induced aggregation as compared with AS1051 obtained in Example 1 <4>.

The amino acid sequence of the recombinant AS1051 obtained as described above was determined as follows. A solution (450 ml) of 2 mM EDTA and 0.1M Tris-HCl (pH 8.5) containing 500 μg of the recombinant AS1051 was added with 1 μl of 4-vinylpyridine, and further added with 15 μg of lysylendopeptidase (produced by Wako Pure Chemical) to perform enzymatic digestion at 37° C. for 3 hours. A digested product was subjected to reverse phase HPLC in the same manner as described in Example 1 <4> to fractionate digested fragment peptides. As a result of amino acid sequence analysis for each of the digested fragment peptides, it was confirmed that the recombinant AS1051 had an amino acid sequence constituted by the sequence of AS1051 shown in SEQ ID NO: 2 and a methionine residue bound to its amino terminal. As for the manner of disulfide bonds, the presence of a disulfide bond between Cys4 and Cys15 was confirmed by mass spectrometry for a fragment peptide containing the both residues. Further, the presence of disulfide bonds between Cys32 and Cys120 and between Cys95 and Cys112 was confirmed by enzymatically digesting fragment peptides comprising the fragments A, B, C shown in FIG. 7 cross-linked through disulfide bonds by using V8 protease (produced by Wako Pure Chemical) (3 μg of V8 protease in a 0.1M ammonium hydrogencarbonate solution), and analyzing amino acid sequences of fragment peptides separated by HPLC using the reverse phase column in the same manner as described in Example 1 <4>.

The decrease in platelets was not observed when the obtained recombinant AS1051 was intravenously administrated to mice in an amount of 1000 μg/kg.

EXAMPLE 3

Production of Anti-Thrombus Single Strand Peptide by Baculovirus/Cultured Insect Cell Expression System The anti-thrombus single strand peptide was produced by expressing the AS1051 gene obtained in Example 2 in a cultured insect cell expression system.

<1> Construction of Baculovirus AS1051 Expression Vector

Figure 13:
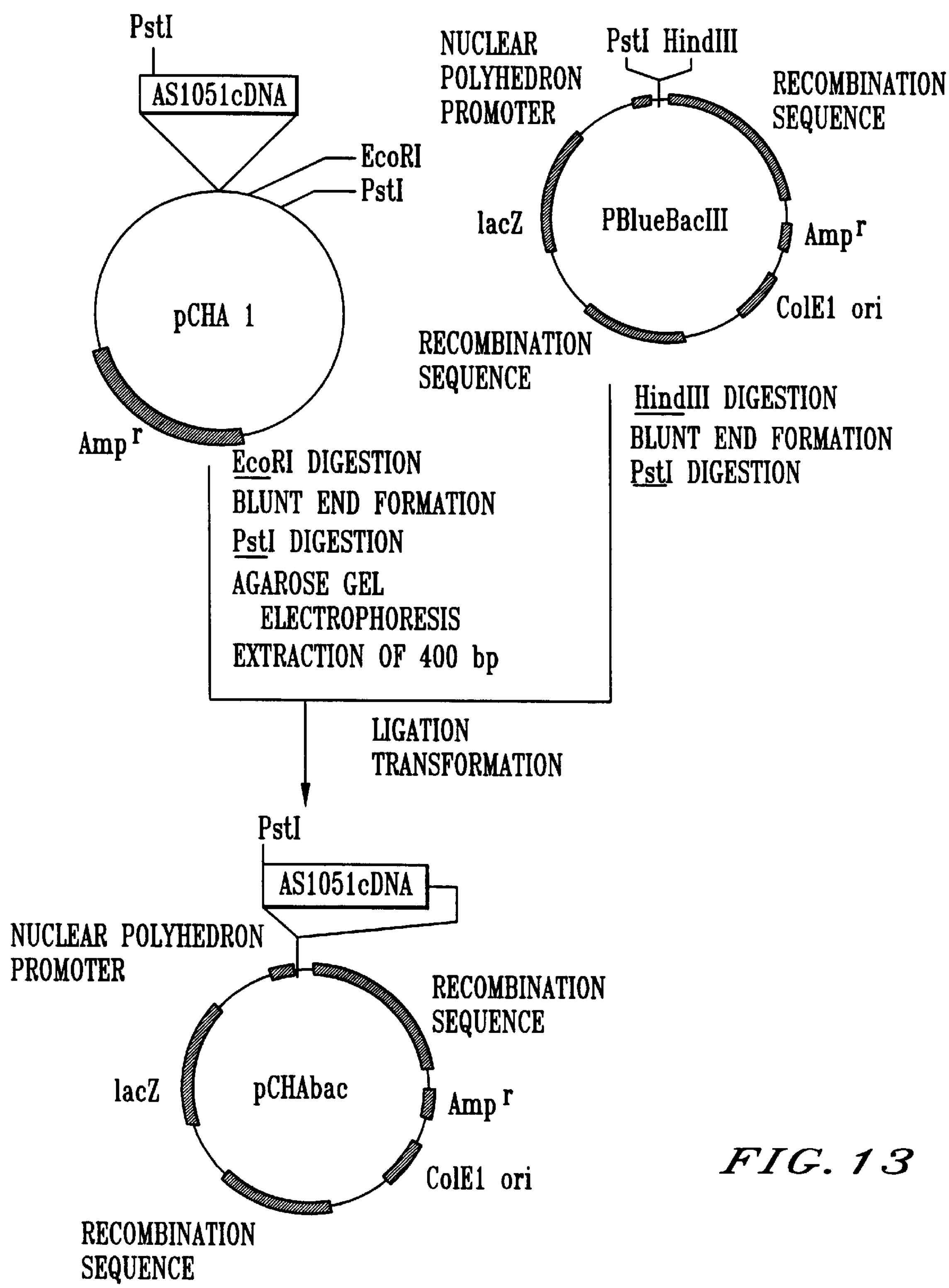
FIG. 13 shows construction steps for an AS1051 expression plasmid pCHAbac for cultured insect cells.

A baculovirus expression system was constructed by using a MaxBac baculovirus expression system (produced by Invitrogen) (see FIG. 13). Namely, pCHA1 obtained in Example 2 was digested with a restriction enzyme EcoRI, and its ends were blunt-ended by using DNA Blunting Kit (produced by Takara Shuzo) in accordance with a protocol of the kit. This fragment was further digested with a restriction enzyme PstI, and digested products were subjected to agarose gel electrophoresis to recover a DNA fragment of 400 base pairs. On the other hand, an expression vector pBlueBacIII was digested with a restriction enzyme HindIII, and its ends were blunt-ended by using DNA Blunting Kit. This fragment was further digested with a restriction enzyme PstI, and digested products were subjected to agarose gel electrophoresis to recover a DNA fragment of 10.3 kilo base pairs. These recovered fragments were ligated by using Ligation Kit, and *E. coli* HB101 was transformed therewith in accordance with the competent cell method to select a transformant on an ampicillin-containing plate. The constructed plasmid was designated as pCHAbac. The construction of the plasmid is shown in FIG. 13.

<2> Transformation of Cultured Insect Cells (Sf9 Strain) with pCHAbac and Preparation of Recombinant Virus Cultured insect cells were transformed and a recombinant virus was obtained in accordance with a protocol of the MaxBac baculovirus expression system (produced by Invitrogen). Namely, DNA (1 μg) of a wild type nuclear polyhedrosis virus (*Autographa californica* nuclear polyhedrosis virus: AcMNPV) and pCHAbac (3 μg) were introduced into cultured insect cells (*Spodoptera frugiperda* 9 strain (Sf9 strain)) in accordance with the liposome method. The virus-introduced cells were cultivated in a TNM—FH (FBS+) culture liquid (produced by Invitrogen) at 27° C. for 48 hours. After that, the culture liquid was recovered to obtain a virus solution.

Cultured insect cells (Sf9 strain) were infected with the virus solution, and cultivated at 27° C. for 7 days on an FNM—FH (FBS+) soft agar medium containing 150 μg/ml of X-gal (5-bromo-4-chloro-3-indolyl-β-D-galactoside). Cells (blue color), which were infected with a virus undergone recombination between the wild type AcMNPV and pCHAbac, were selected. The cells were picked up from the plate by using a Pasteur pipet, and Sf9 cells were infected therewith again after appropriate dilution. The purifying operation as described above was repeated twice to obtain a virus solution in which only the recombinant virus was present.

<3> Expression of AS1051 Peptide by Baculovirus/cultured Insect Cell Expression System The AS1051 peptide was expressed by using the recombinant virus. Sf9 cells ($6\times10^6$ cells) were inoculated to 10 ml of an FNM—FH (FBS+) culture liquid in a flask for cell culture (NUNCLON 260 ml, bottom area: 75 $cm^2$, produced by Nunc), and the purified recombinant virus ($3\times10^6$ cfu) was added thereto to perform cultivation at 27° C. for 24 hours. After that, the culture liquid was removed from the flask to which 10 ml of an FNM—FH (FBS—) culture liquid containing no fetal bovine serum was added to perform further cultivation at 27° C. for 7 days. After completion of the cultivation, 4 ml of the culture liquid was collected, which was concentrated into 400 μl by using Centricon 10 (produced by Amicon) to obtain a culture supernatant concentrate (10-fold concentrated solution).

On the other hand, a buffer (30 mM Tris-HCl pH 7.5, 10 mM EDTA, 30 mM sodium chloride) was added to the flask from which the culture liquid had been removed. Cells were exfoliated from flask walls by pipetting. After that, a cell suspension was recovered, and centrifuged to wash the cells once. The cells were subsequently resuspended in 2 ml of the buffer. This cell suspension was treated with a ultrasonic disrupter Insonator 200M (produced by Kubota) at 180 W for 5 minutes to disrupt the cells. After the disruption, centrifugation was performed at 10,000×G for 30 minutes, and a supernatant was recovered to obtain a cell-disrupted solution. Control sample were also provided by cultivating Sf9 cells infected with the wild type AcNMPV virus and Sf9 cells infected with no virus under the same condition as described above for sample preparation.

The culture supernatant concentrate (5 μl) and the cell-disrupted solution (10 μl) prepared as described above were subjected to SDS-polyacrylamide gel electrophoresis respectively under a reduced condition with addition of 1% mercaptoethanol, followed by staining with Coomassie Brilliant Blue (CBB). As a result, a protein was detected at a position of 15 kilodaltons in considerable amounts in both of the culture supernatant concentrate and the cell-disrupted solution obtained from the cells infected with the recombinant virus. On the contrary, no protein could be detected at the position of 15 kilodaltons in both of the controls including the culture supernatant concentrate and the cell-disrupted solution obtained from the Sf9 cells only, and those obtained from the Sf9 cells infected with the wild type virus AcMNPV. It is noted that the value of the molecular weight of 15 kilodaltons coincides with the molecular weight of AS1051 purified from the crude snake venom.

<4> Activity of AS1051 Peptide Produced by Baculovirus/Cultured Insect Cell Expression System The recombinant protein in cultured insect cells and the recombinant protein in culture supernatant obtained as described above provided the inhibition on the binding of von Willebrand factor with platelets induced by botrocetin, as measured by the following method.

Formalin-fixed platelets were prepared as follows. Fresh blood collected from healthy human added with 1/10 volume of 3.8% sodium citrate was centrifuged at 900 rpm for 15 hours to obtain human platelet rich plasma (PRP) to which a 0.15M sodium chloride aqueous solution having the same volume and containing 20 mM phosphate buffer (pH 7.4) dissolved with 2% paraformaldehyde was added, followed by being stored at 4° C. overnight stationarily and. After the storage, platelets were recovered by centrifugation, and they were washed twice with a 0.15M sodium chloride aqueous solution containing 20 mM phosphate buffer (pH 7.4). After the washing, the fixed platelets were suspended in the same solution, and stored.

A test to measure the inhibition on the binding of $^{125}$I-labeled von Willebrand factor with fixed platelets was performed by using the fixed platelets obtained as described above in accordance with the method of Chopek et al. (M. W. Chopek et al., *Biochemistry,* 25, 3146–3155 (1986)). Namely, a suspension of the prepared fixed platelets was added with a sample for measurement, botrocetin, and $^{125}$I-labeled von Willebrand factor, and reacted at room temperature for 30 minutes to measure the amount of von Willebrand factor bound with the platelets by using a γ-counter (Packard Multi-Prias, produced by Packard). In this measurement, the reaction solution had a volume of 50 μl including 5 μl of the added sample for measurement.

Figure 14:
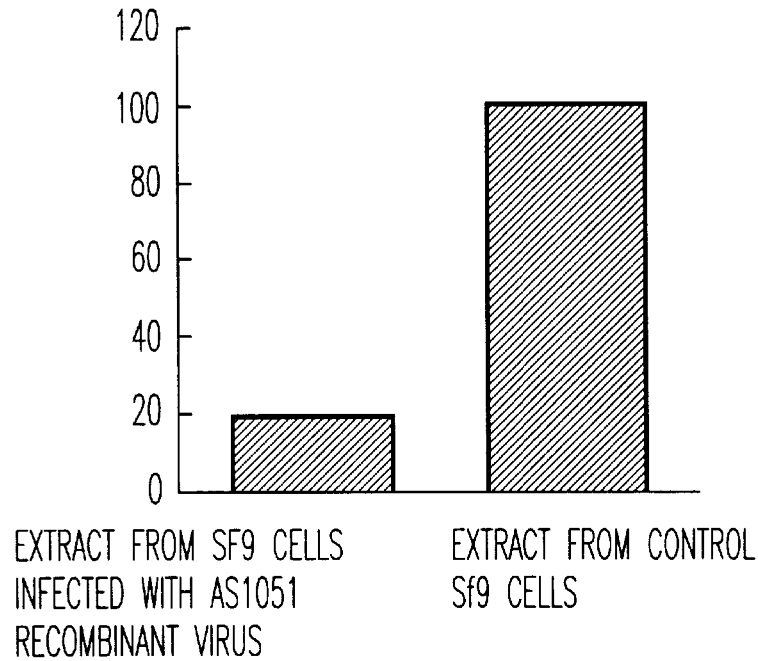
FIG. 14 shows an inhibiting activity of AS1051 in a cell-disrupted solution expressed by cultured insect cells on binding of von Willebrand factor with fixed platelets evoked by botrocetin.
Figure 15:
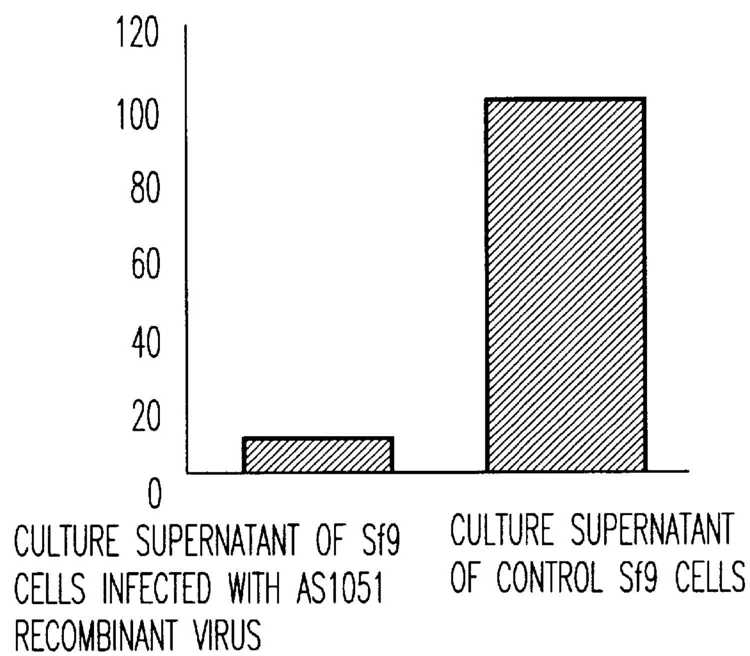
FIG. 15 shows an inhibiting activity of AS1051 in a culture supernatant expressed by cultured insect cells on binding of von Willebrand factor with fixed platelets evoked by botrocetin.

FIG. 14 shows a result of measurement of the inhibiting activity on the binding of von Willebrand factor with the platelets induced by botrocetin with respect to cell-disrupted solutions prepared from the Sf9 cells infected with the AS1051 recombinant virus and the control Sf9 cells in accordance with the method described above. FIG. 15 shows a result of measurement of the inhibiting activity on the binding of von Willebrand factor with the platelets induced by botrocetin with respect to culture supernatant concentrates (3-fold concentrated solutions) prepared from the Sf9 cells infected with the AS1051 recombinant virus and the control Sf9 cells in accordance with the method described above. As clarified from these results, the cell-disrupted solution and the cultured cell supernatant obtained from the cells infected with the recombinant virus almost completely inhibited the binding of von Willebrand factor to the platelets. According to this fact, it was revealed that the AS1051 peptide to be produced by the baculovirus/cultured insect cell expression system as an intracellular soluble protein and an extracellular secretion protein has the activity to inhibit the binding between platelets and von Willebrand factor.

EXAMPLE 4

Production of Anti-Thrombus Single Strand Peptide by Cultured Animal Cell Expression System The anti-thrombus single strand peptide was produced by expressing the AS1051 gene in a cultured animal cell expression system by using CHO cells.

Figure 16:
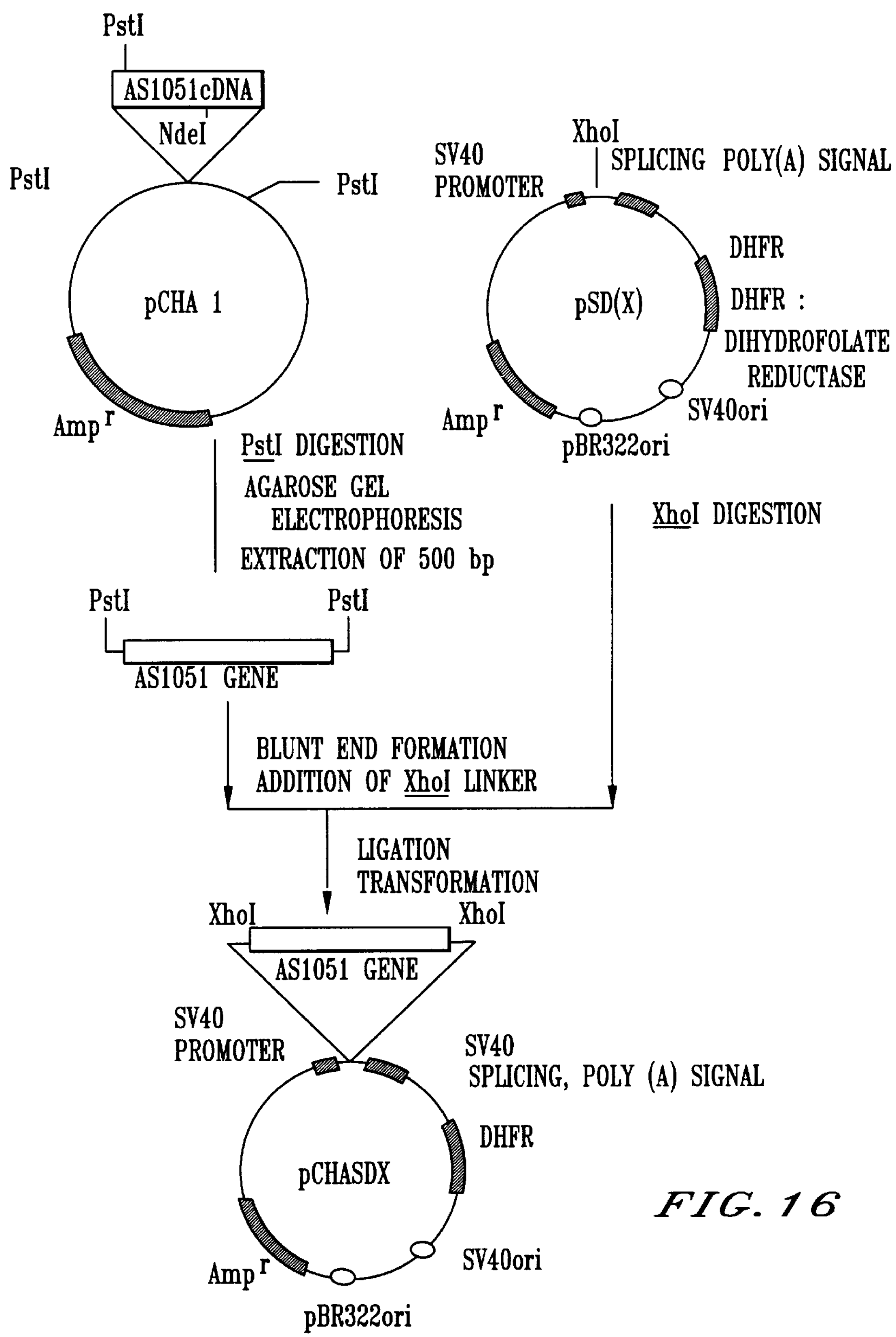
FIG. 16 shows construction steps for an AS1051 expression plasmid pCHASDX for cultured animal cells (CHO cells).

The AS1051 gene was excised by digesting pCHA1 with a restriction enzyme PstI. Both ends of an obtained DNA fragment were blunt-ended with DNA Blunting Kit (produced by Takara Shuzo). An XhoI linker (produced by Takara Shuzo) was ligated to the both ends. This DNA fragment was digested with a restriction enzyme XhoI, and then subjected to agarose gel electrophoresis to extract a DNA fragment of 500 base pairs. The DNA fragment was inserted into an XhoI site of a CHO cell expression vector pSD(X) (M. Murata et al., *Proc. Natl. Acad. Sci. U.S.A.,* 85, 2434–2438 (1988)). It is noted that this vector pSD(X) can express a foreign gene in CHO cells, the vector comprising replication origins of pBR322 and SV40, an ampicillin resistance gene, and a methotrexate resistance gene, and the vector further comprising an SV40 promoter, an SV40 splicing signal, and a poly(A) addition signal. The construction process of the plasmid described above is shown in FIG. 16.

*Escherichia coli* HB101 was transformed with pSD(X) harboring the inserted AS1051 gene to obtain a transformant. An expression plasmid, in which the AS1051 gene was inserted in a desired direction with respect to the vector, was obtained from the transformant. The plasmid was designated as pCHASDX. The plasmid pCHASDX was used to transform a dihydrofolate reductase-deficient strain of CHO cells in accordance with the calcium phosphate method ("Current Protocols in Molecular Biology", Green Publishing Associates). Transformants were cultivated in a medium containing alpha-MEM (nucleic acid minus) (produced by GIBCO), 10% fetal bovine serum (FCS), and methotrexate 0.05 μM. Thus transformants harboring the expression plasmid incorporated in chromosome were selectively grown.

Obtained strains were cultivated by increasing the concentration of methotrexate in the medium stepwise up to 0.5 μM to select methotrexate-resistant strains. Thus a strain was obtained in which the AS1051 gene was considered to be amplified on chromosome of CHO cells. A single clone of this strain was proliferated to obtain cells. Total RNA was extracted from the cells by using ISOGEN kit (produced by Nippon Gene). The AS1051 gene was amplified by using primers CHA16Y (SEQ ID NO: 13) and CHA115Q (SEQ ID NO: 14) in accordance with the RT-PCR method in the same manner as described in Example 2 <2>. Amplified DNA was analyzed by agarose gel electrophoresis. As a result, it was detected that a DNA fragment having a size postulated from the nucleotide sequence of the AS1051 gene was amplified. Thus it was confirmed that mRNA of the AS1051 gene was transcribed in CHO cells. The cells were used to investigate expression of the AS1051 peptide. Namely, the cells (2×104 cells) were cultivated for 4 days in 5 ml of a medium containing alpha-MEM (nucleic acid minus), 10% fetal bovine serum, and methotrexate 0.5 μM. After that, the medium was exchanged with a serum-free medium AS104 (produced by Ajinomoto) containing methotrexate 0.5 μM, followed by cultivation for further 3 days.

Figure 17:
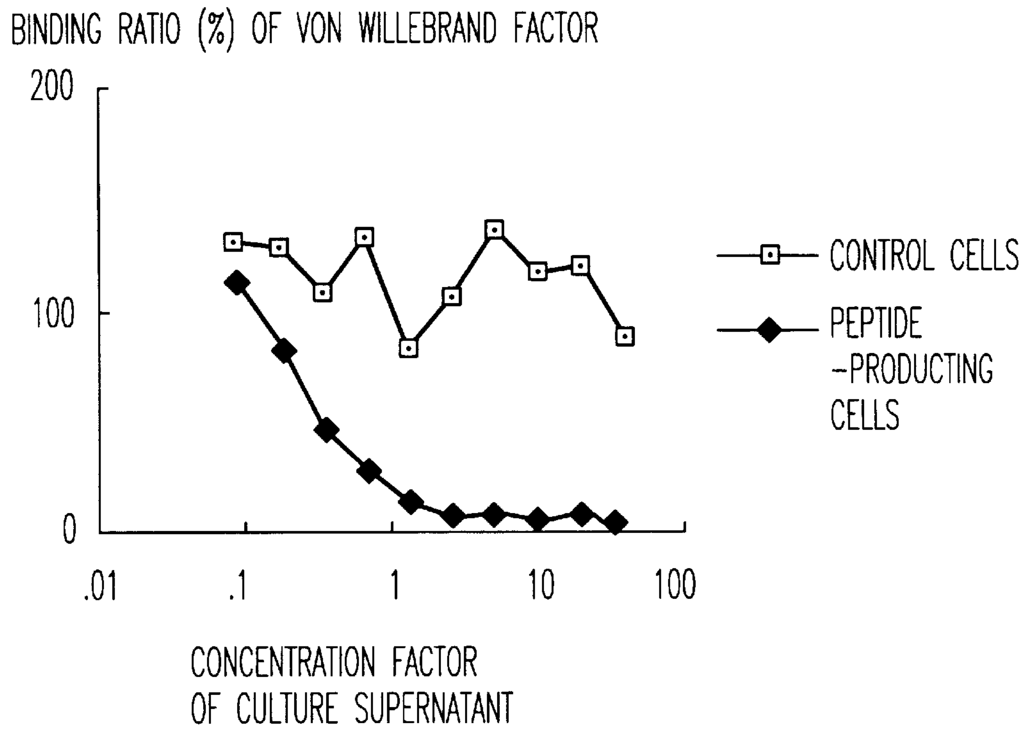
FIG. 17 shows an inhibiting activity of AS1051 in a culture supernatant expressed by CHO cells on binding of von Willebrand factor with fixed platelets evoked by ristocetin.
Figure 18:
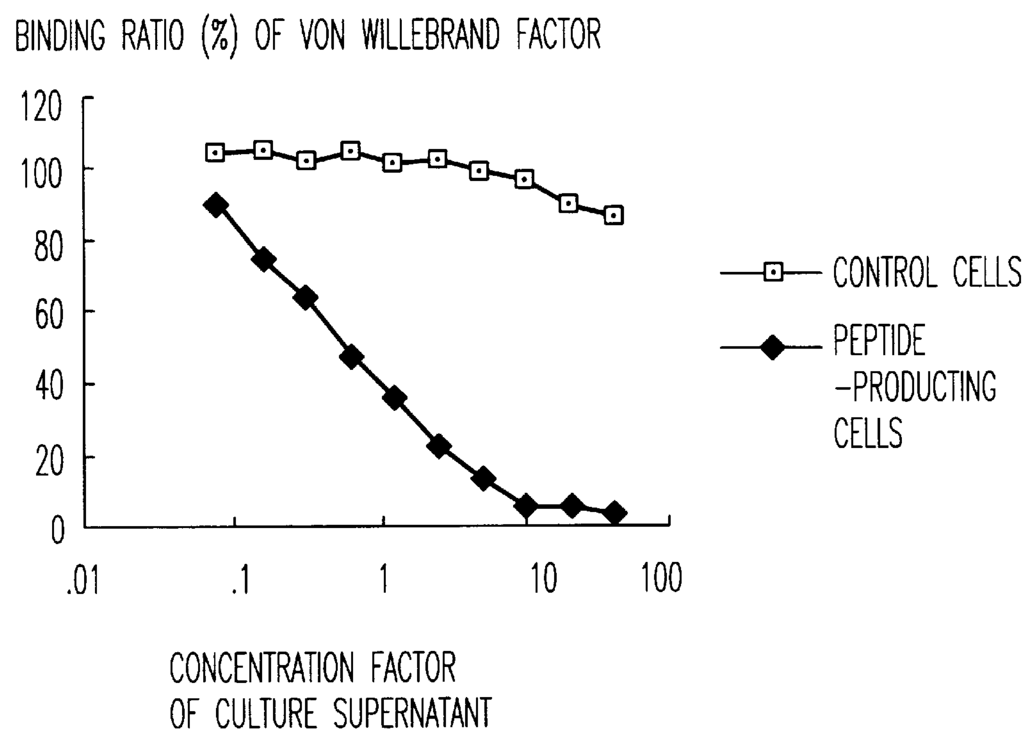
FIG. 18 shows an inhibiting activity of AS1051 in a culture supernatant expressed by CHO cells on binding of von Willebrand factor with fixed platelets evoked by botrocetin.

The medium was recovered after completion of the cultivation, and 4 ml of the medium was concentrated into 100 μl by using Centricon-10 (produced by Amicon) to obtain a concentrate. The concentrate was successively diluted to measure the activity to inhibit the binding of von Willebrand factor with platelets evoked by ristocetin and botrocetin in accordance with the method described in Example 3<4>. FIGS. 17 and 18 show the inhibiting activities of solutions obtained by concentrating or diluting, into predetermined concentrations, the culture supernatants of AS1051 peptide-producing cells and control cells which did not produce the AS1051 peptide. As shown in FIGS. 17 and 18, it was demonstrated that the inhibiting activity of the culture supernatant of the peptide-producing cells depended on the concentration, and the active AS1051 was contained.

EXAMPLE 5

Production of Mutant AS1051 Peptide

*Escherichia coli* was allowed to express an AS1051 peptide having mutation (hereinafter referred to as "Cys81Ala mutation") to substitute an alanine residue for an 81th cysteine residue as counted from the N-terminal (except for the methionine residue to initiate translation) in order to investigate the activity to inhibit the binding of von Willebrand factor with platelets.

<1> Production of Cys81Ala Mutant Peptide

Figure 19:
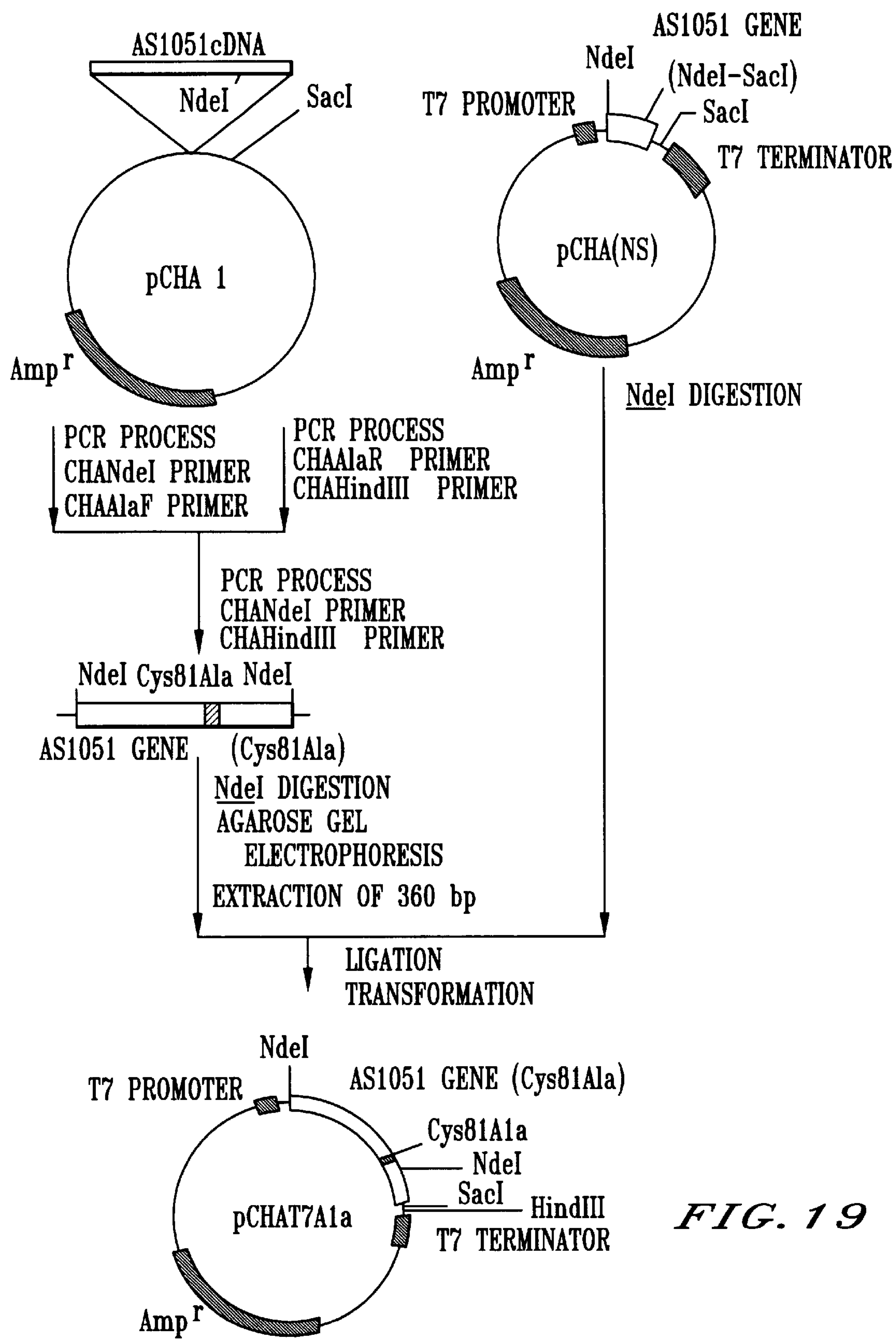
FIG. 19 shows construction steps for a plasmid pCHAT7Ala for expressing, in *Escherichia coli*, AS1051 having mutation to substitute an alanine residue for an 81th cysteine residue as counted from the N-terminal (except for methionine residue for translation initiation).

Mutation was introduced into the AS1051 gene so that the cysteine residue, which did not participate in disulfide bond formation of the AS1051 peptide (81th cysteine residue in SEQ ID NO: 2), was substituted with alanine in accordance with the site-directed mutagenesis for nucleotide sequence described in "PCR Protocol" (published by Academic Press). pCHA1 was used as a template to perform the PCR process by using the primer CHANdeI (SEQ ID NO: 9) synthesized in Example 2 and a newly synthesized primer CHAAlaF (SEQ ID NO: 11), or by using a newly synthesized primer CHAAlaR (SEQ ID NO: 12) and the primer CHAHindIII (SEQ ID NO: 10) synthesized in Example 2. Respective reaction products were subjected to agarose gel electrophoresis, and amplified DNA fragments were extracted from the gel. These DNA fragments were used as templates to perform the second PCR process by using the primers CHANdeI and CHAHindIII to prepare a mutant gene. PCR-amplified DNA fragments were digested with a restriction enzyme NdeI, followed by agarose gel electrophoresis to extract a DNA fragment of 360 bp from the gel. This DNA fragment was inserted into an NdeI site of PCHA(NS) having been digested with the restriction enzyme NdeI. The plasmid construction process described above is shown in FIG. 19.

The plasmid prepared as described above was used to transform *Escherichia coli* HB101 in accordance with the competent cell method. Transformants were selected on an ampicillin-containing plate. Plasmids were prepared from the transformants in accordance with the alkaline SDS method. Nucleotide sequences were determined in accordance with the method described in Example 8 by using T7 primer and SP6 primer (produced by Stratagene). Thus a plasmid, in which the objective mutation was introduced, was selected. The obtained expression vector was designated as pCHA7Ala. pCHA7Ala was used to transform *Escherichia coli* JM109(DE3) to obtain a transformant. The AS1051 peptide having the Cys81Ala mutation was expressed and produced by cultivating the transformant in the same manner as in Example 2<4>. Bacterial proteins were subjected to SDS-polyacrylamide gel electrophoresis. As a result, it was confirmed that the recombinant peptide could be produced and accumulated as inclusion bodies in cells of *Escherichia coli* in approximately the same amount as that of the genetically recombined wild type AS1051 peptide produced in Example 2 <4>.

Figure 20:
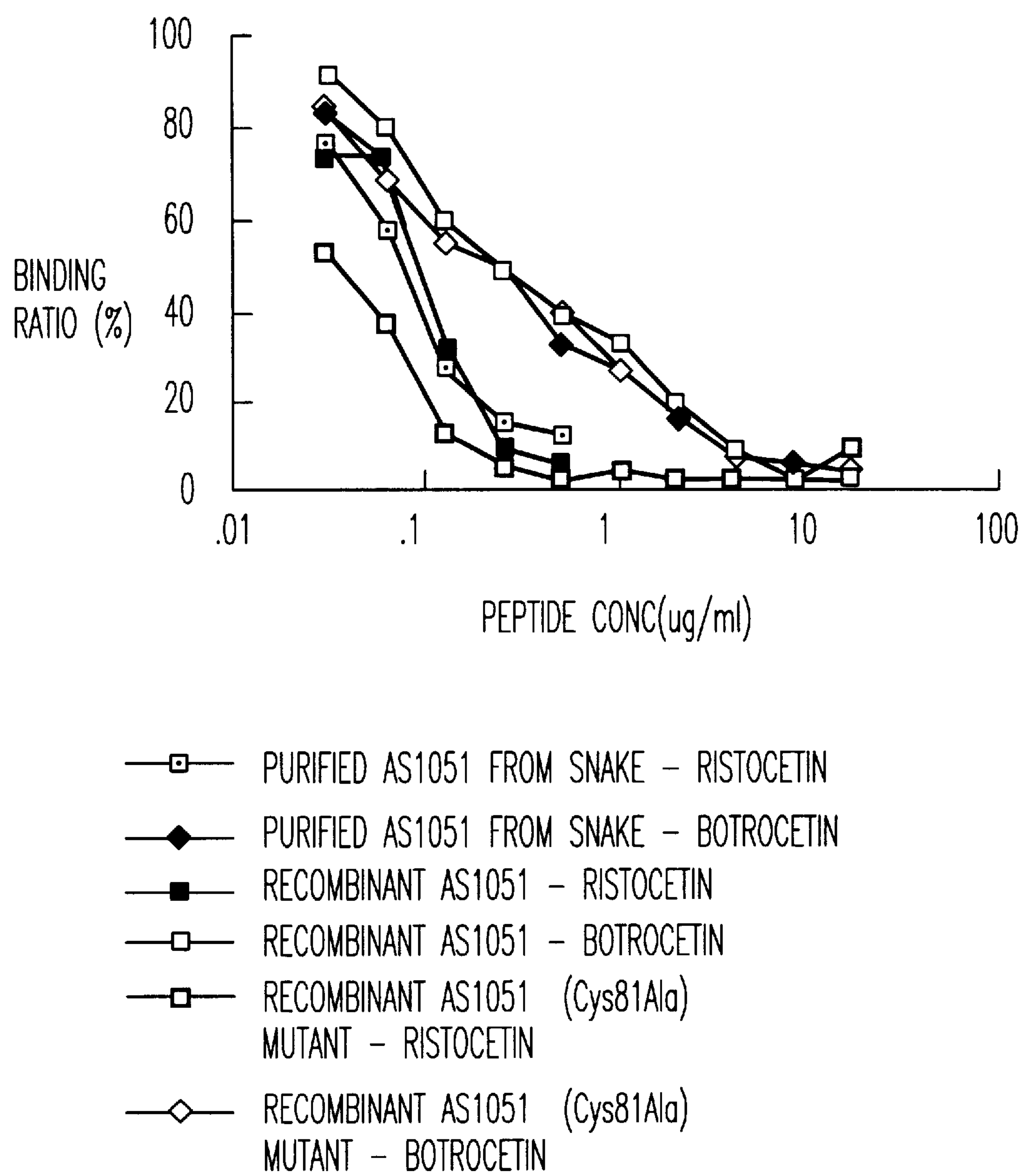
FIG. 20 shows inhibiting activities of AS1051 prepared from a snake venom, AS1051 produced by *Escherichia coli*, and AS1051 (Cys81Ala mutant AS1051) with an alanine residue substituted for an 81th cysteine residue as counted from the N-terminal, on binding of von Willebrand factor with fixed platelets evoked by ristocetin or botrocetin.

<2> Solubilization and Activation of Inclusion Bodies of Cys81Ala Mutant AS1051 Peptide The inclusion bodies were solubilized and activated in accordance with the method described in Example 2<4>. An obtained purified protein exhibited the same molecular weight as the molecular weight of AS1051 shown in Example 1<4> according to SDS electrophoresis. It was also confirmed that the purified protein had the same manner of disulfide bonds as that of AS1051. The activity to inhibit platelet aggregation was measured for the obtained Cys81Ala mutant peptide in accordance with the same method as described in Example 1<5>. As a result, the mutant peptide did not inhibit the ADP-induced aggregation and the collagen-induced aggregation, and it inhibited the ristocetin-induced aggregation and the botrocetin-induced aggregation at approximately the same degree as that of AS1051. The mutant peptide exhibited the inhibiting activity equivalent to those of AS1051 obtained in Example 1<4> and recombinant AS1051 obtained in Example 2<4> on the binding of von Willebrand factor with the fixed platelets induced by ristocetin or botrocetin (FIG. 20). The mutant AS1051 peptide thus obtained was stable in storage in a solution at 30° C. and dialysis at 4° C., while the recombinant AS1051 peptide was somewhat insolubilized in storage in a solution at 30° C. on dialysis at 4° C. According to this result, it is considered that the recombinant mutant AS1051 peptide has higher stability than the recombinant AS1051 peptide.

EXAMPLE 6

Production of Shortened AS1051 Peptides

AS1051 peptides having shortened N-terminal portions and/or a shortened C-terminal portion were expressed in *Escherichia coli* to investigate the activities of the shortened AS1051 peptides to inhibit the binding of von Willebrand factor with platelets.

<1> Production of Shortened AS1051 Peptides

Figure 21:
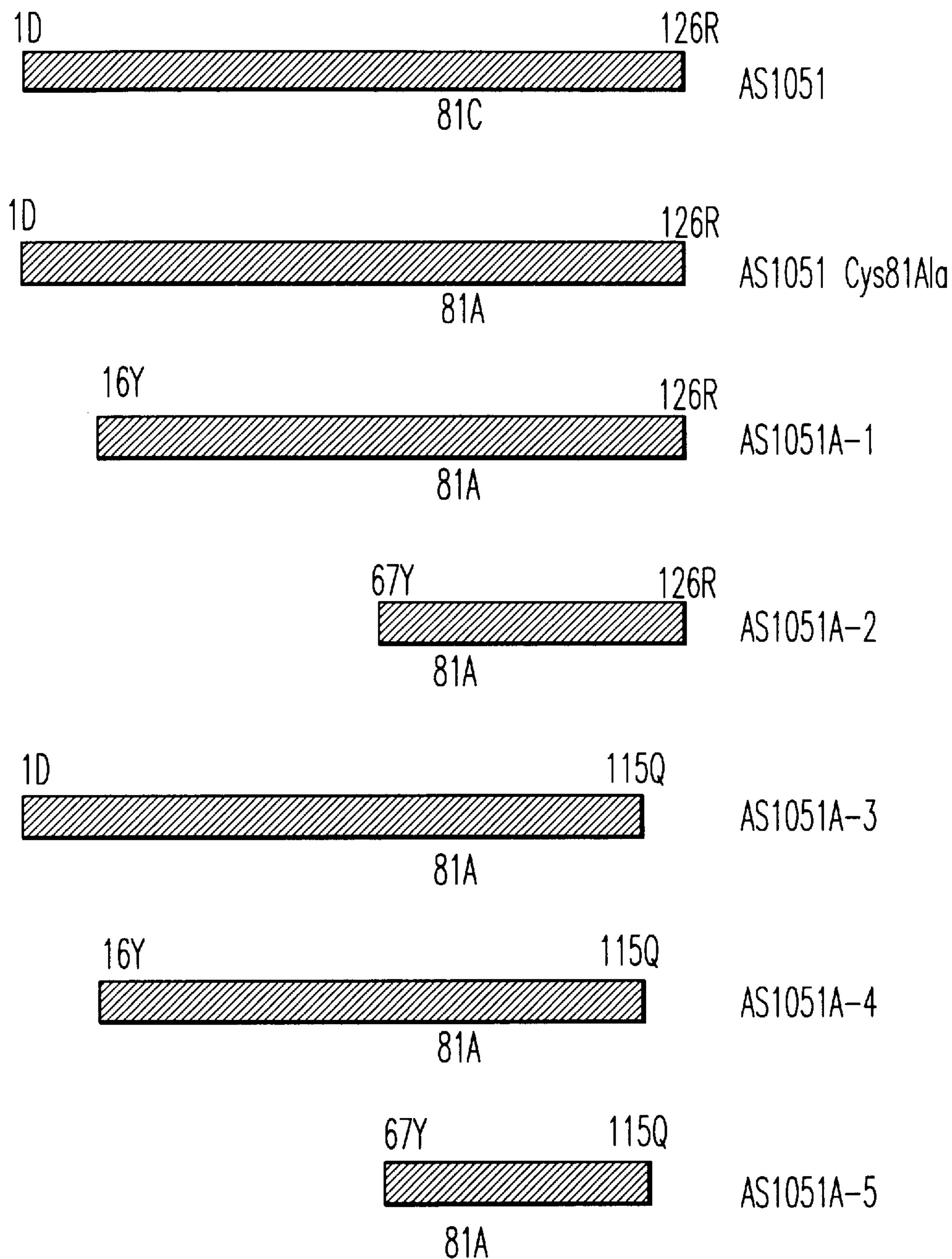
FIG. 21 schematically shows structures of various shortened AS1051 peptides.

Expression systems for peptides were constructed starting from the AS1051 peptide having the Cys81Ala mutation (hereinafter referred to as "AS1051Cys81Ala peptide"), the constructed peptides being deficient in 15 amino acid residues or 65 amino acid residues having been located on an N-terminal region and/or 11 amino acid residues having been located on a C-terminal region. Namely, the produced peptides were five species including a peptide (AS1051A-1) having a sequence from a 16th tyrosine residue to a 126th arginine residue, a peptide (AS1051A-2) having a sequence from a 67th tyrosine residue to the 126th arginine residue, a peptide (AS1051A-3) having a sequence from a 1st aspartic acid residue to a 115th glutamine residue, a peptide (AS1O51A-4) having a sequence from the 16th tyrosine residue to the 115th glutamine residue, and a peptide (AS1051A-5) having a sequence from the 67th tyrosine residue to the 115th glutamine residue. Structures of these peptides are schematically shown in FIG. 21. The numbers of amino acids were counted while excluding methionine for initiation of translation, the numbers indicating amino acid numbers in the amino acid sequence shown in SEQ ID NO: 2.

Expression plasmids for the shortened AS1051 peptides were constructed as follows. pCHAT7Ala was used as a template to perform the PCR process by using primers CHA16Y (SEQ ID NO: 13) and CHAHindIII (SEQ ID NO: 10) for AS1051A-1, using primers CHA67Y (SEQ ID NO: 15) and CHAHindIII for AS1051A-2, using primers CHANdeI (SEQ ID NO: 9) and CHA115Q (SEQ ID NO: 14) for AS1O51A-3, using primers CHA16Y and CHA115Q for AS1051A-4, and using primers CHA67Y and CHA115Q for AS1051A-5.

As for amplified products obtained by using the primers CHA16Y and CHAHindIII and the primers CHA67Y and CHAHindIII, the respective amplified products were digested with NdeI, and subjected to agarose gel electrophoresis to extract DNA fragments of 310 base pairs and 160 base pairs respectively. The respective DNA fragments were inserted into an NdeI site of pCHA(NS). Obtained recombinant plasmids were used to transform *E. coli* HB101 in accordance with the calcium chloride method, and transformants were selected on ampicillin-containing plates. Objective transformants, in which the respective amplified DNA fragments were inserted in objective directions with respect to the plasmids, were selected from the transformants. An expression plasmid thus obtained having the inserted fragment of 310 base pairs was designated as pCHAT7Ala (16Y126R), and an expression plasmid thus obtained having the inserted fragment of 160 base pairs was designated as pCHAT7Ala(67Y126R).

As for amplified products obtained by using the primers CHANdeI and CHA115Q, the primers CHA16Y and CHA115Q, and the primers CHA67Y and CHA115Q, the respective amplified products were digested with NdeI and HindIII, and subjected to agarose gel electrophoresis to extract DNA fragments of 360 base pairs, 310 base pairs, and 160 base pairs respectively. The respective DNA fragments were ligated with pCHA(NS) having been digested with NdeI and HindIII. Obtained recombinant plasmids were used to transform *E. coli* HB101 in accordance with the calcium chloride method, and transformants were selected on ampicillin-containing plates. An expression plasmid thus obtained having the inserted fragment of 360 base pairs was designated as pCHAT7Ala(1D115Q), an expression plasmid thus obtained having the inserted fragment of 310 base pairs was designated as pCHAT7Ala(16Y115Q), and an expression plasmid thus obtained having the inserted fragment of 160 base pairs was designated as pCHAT7Ala(67Y115Q).

The five species of the expression plasmids for the shortened AS 1051 peptides were used to transform *E. coli*

JM09(DE3) to obtain transformants respectively. These transformants were cultivated in the same manner as the method described in Example 2, and bacterial cells after the cultivation were microscopically observed. As a result, it was confirmed that all of the five species of the transformants formed inclusion bodies. Bacterial proteins of the respective transformants were analyzed by SDS-polyacrylamide gel electrophoresis. As a result, considerable amounts of proteins were found at positions of molecular weights postulated from the respective amino acid sequences of the shortened AS10151 peptides.

Figure 22:
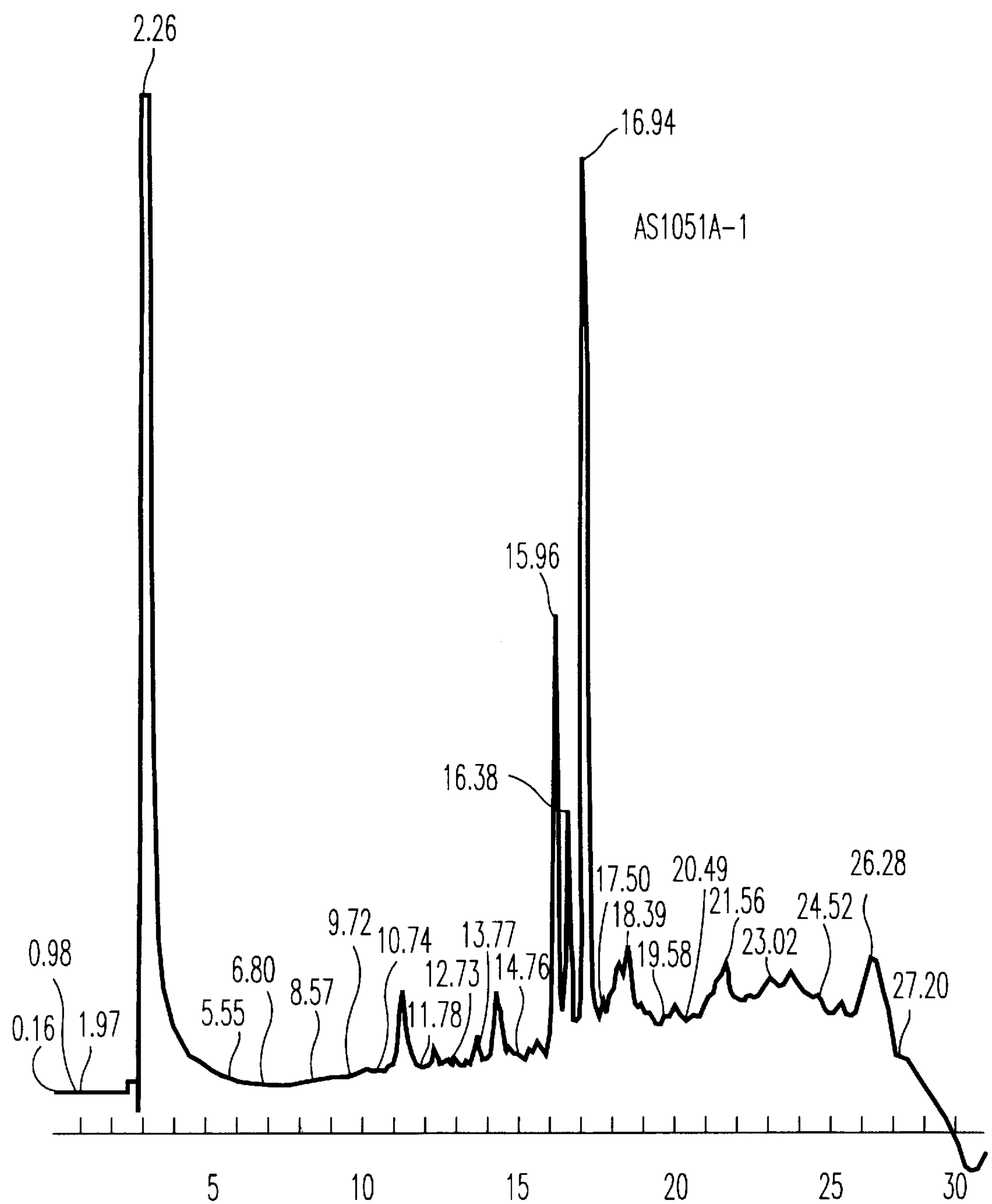
FIG. 22 shows an HPLC chromatogram of AS1051A-1.
Figure 23:
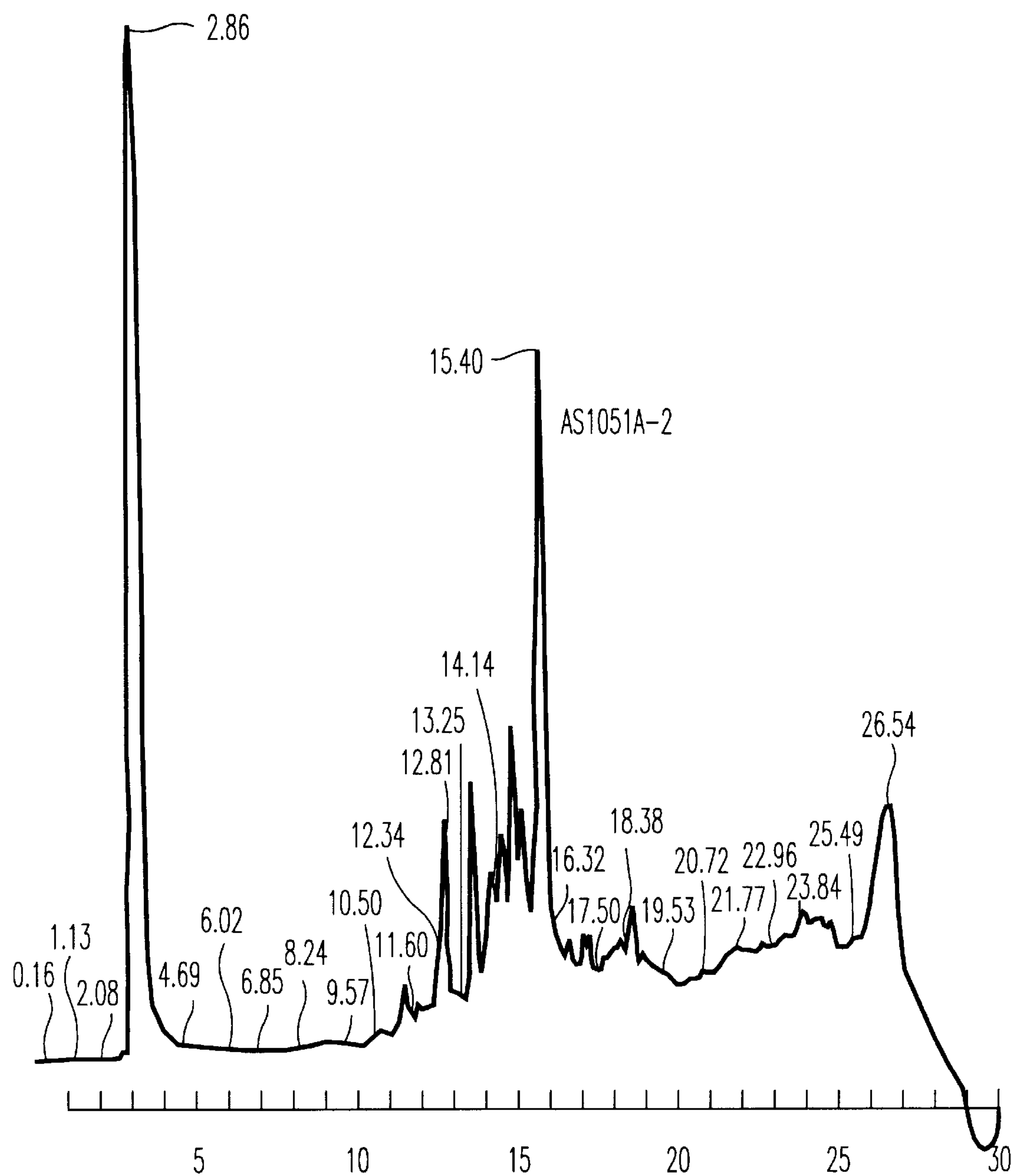
FIG. 23 shows an HPLC chromatogram of AS1051A-2.
Figure 24:
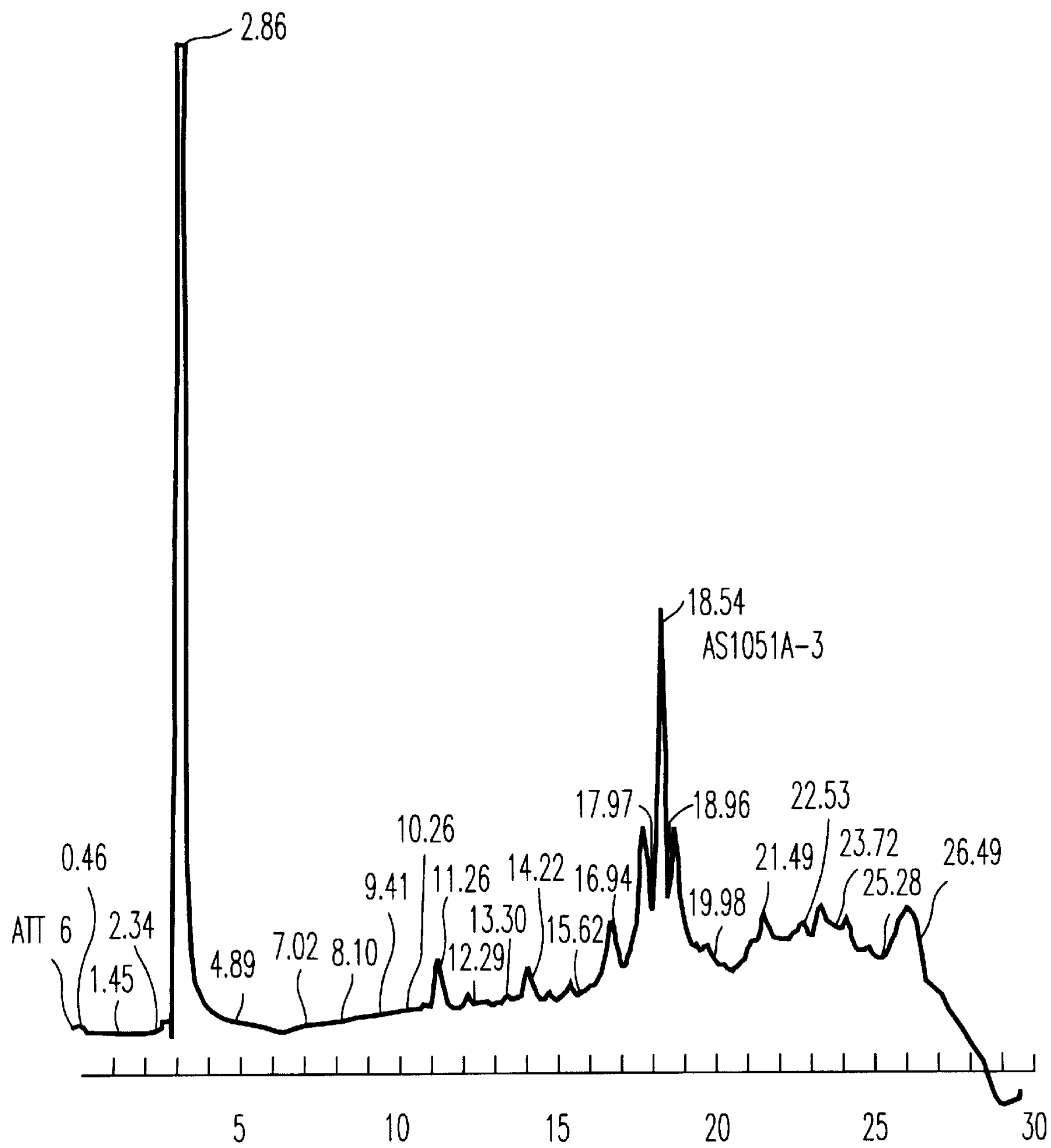
FIG. 24 shows an HPLC chromatogram of AS1051A-3.
Figure 25:
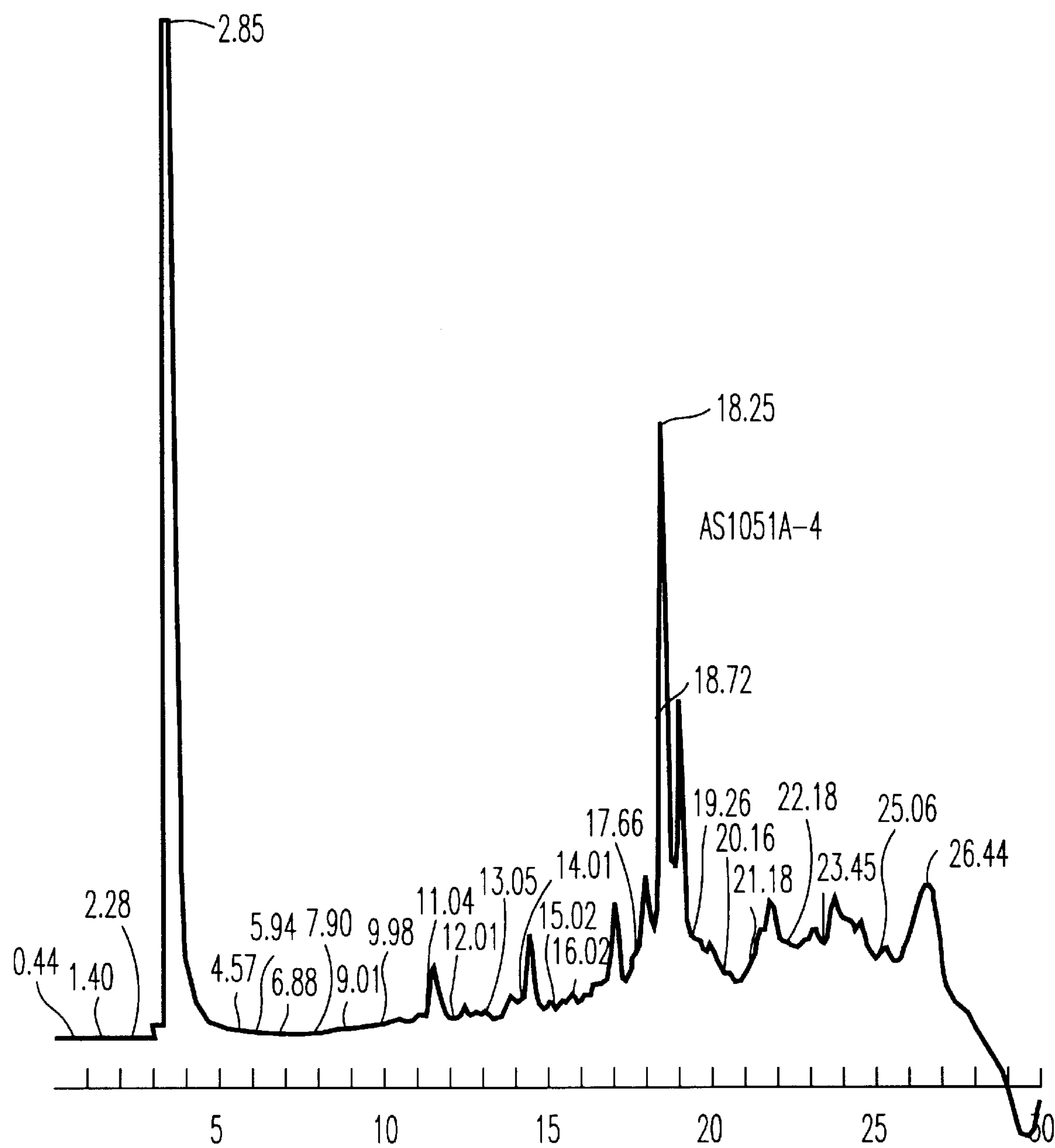
FIG. 25 shows an HPLC chromatogram of AS1051A-4.
Figure 26:
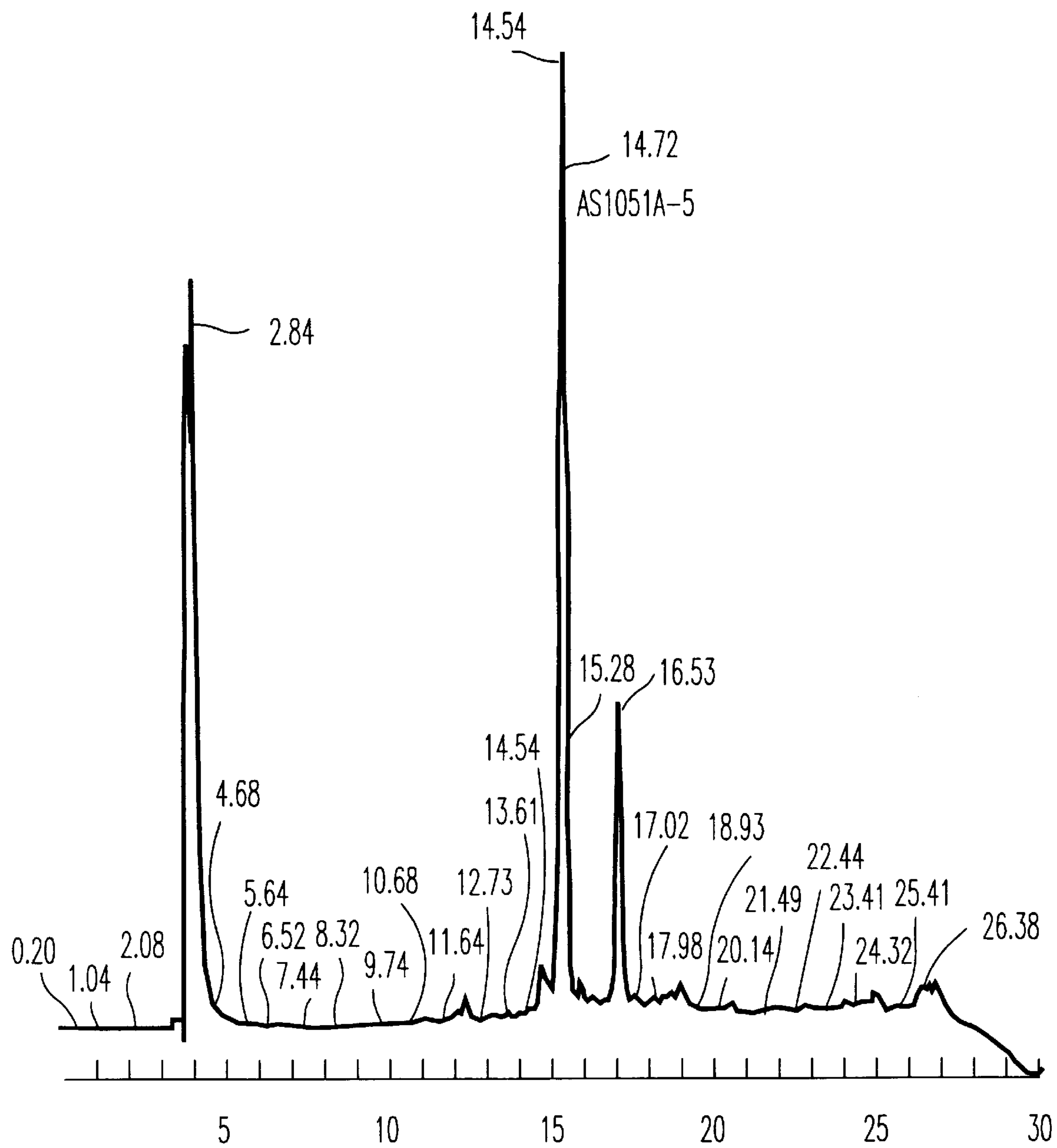
FIG. 26 shows an HPLC chromatogram of AS1051A-5.

The inclusion bodies were prepared from the respective transformants in the same manner as described in Example 2. The inclusion bodies were dissolved in 286 μl of a 7M guanidine hydrochloride solution containing 10 mM EDTA and 0.5M Tris-HCl (pH 8.5), and then stored at 4° C. overnight. After that, each of aliquots (10 μl) was applied to high-performance liquid chromatography by using an SSC-VP318–1251 column (diameter: 4.6 mm, length: 250 mm, produced by Senshu Kagaku). Elution was performed by using a concentration gradient from an acetonitrile concentration of 31% to a concentration of 52% containing 0.1% trifluoroacetic acid. As a result, peaks originating from the inclusion bodies were obtained as shown in FIG. 22 (AS1051A-1), FIG. 23 (AS1051A-2), FIG. 24 (AS1051A-3), FIG. 25 (AS1051A-4), and FIG. 26 (AS1051A-5) respectively.

Figure 27:
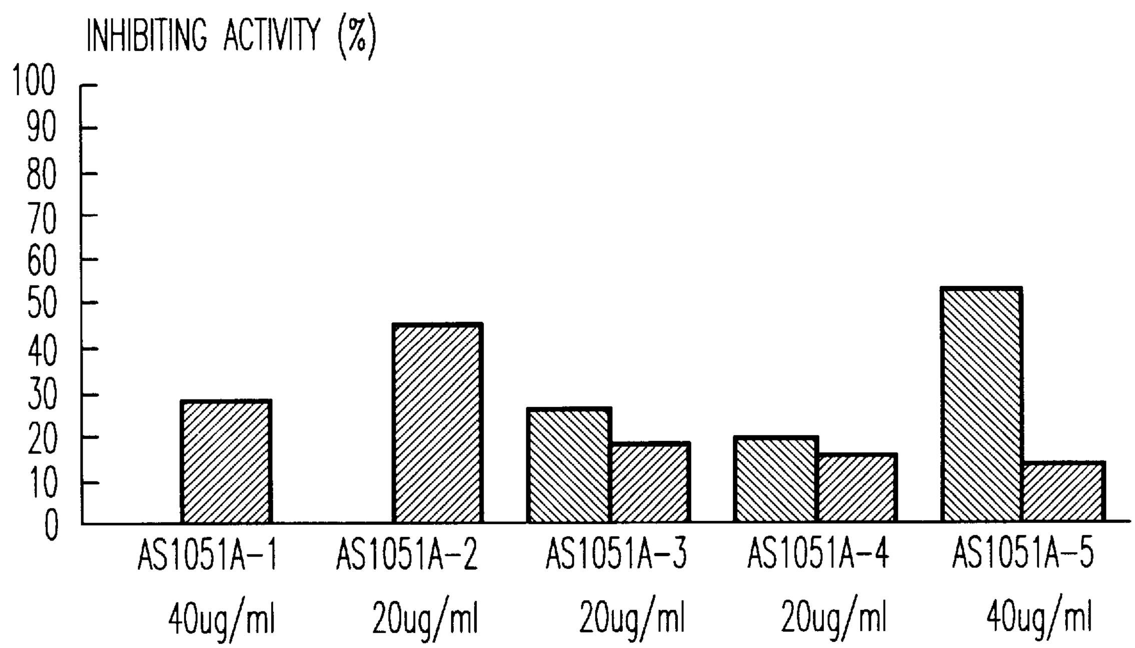
FIG. 27 shows inhibiting activities of the various shortened AS1051 peptides on binding of von Willebrand factor with fixed platelets evoked by ristocetin or botrocetin.

Remaining entire amounts of AS1051A-1, AS1O51A-2, AS1051A-3, AS1051A-4, and AS1051A-5 dissolved in the 7M guanidine hydrochloride solution and stored overnight as described above were made to have acidic pH adjusted with trifluoroacetic acid. After that, they were fractionated and collected by HPLC with a reverse phase column (Vydac 214TP1022, produced by Vydac, diameter: 22 mm, length: 250 mm) at a flow rate of 15 ml in accordance elution with a concentration gradient (20 minutes) from an acetonitrile concentration of 30% to a concentration of 60% containing 0.1% trifluoroacetic acid. Obtained respective peptides were added with bovine serum albumin in 10-fold amounts of the peptide, lyophilized, and dissolved in a physiological saline solution. These solutions were used as samples to measure the activity to inhibit the binding of von Willebrand factor with formalin-fixed platelets induced by botrocetin or ristocetin in the same manner as the method described in Example 1<5>. Results are shown in FIG. 27. As shown in FIG. 27, all of the shortened AS1051 peptides clearly exhibited the binding-inhibiting activity at concentrations shown in FIG. 27.

Industrial Applicability

The present invention provides the peptide which inhibits the binding of von Willebrand factor with platelets without causing the decrease in platelets, although the peptide is obtained from a peptide originating from a snake venom which causes the decrease in platelets upon in vivo administration, provided that the binding closely participates in crisis of thrombosis. Accordingly, it is possible to provide a pharmaceutical composition which is hopeful as an anti-thrombosis drug.

What is claimed is:

1. An isolated and purified monomeric polypeptide comprising:

(1) the amino acid sequence from residue 67 to residue 115 of SEQ ID NO: 2, or (2) the amino acid sequence from residue 67 to residue 115 of SEQ ID NO: 2 in which the cysteine residue at position 81 of SEQ ID NO: 2 is substituted with an amino acid other than cysteine, wherein the polypeptide has at least one disulfide bond between two cysteine residues in the amino acid sequence.

2. The polypeptide of claim 1, which has a disulfide bond between the cysteine residues at positions 95 and 112 of SEQ ID NO: 2.

3. The polypeptide of claim 2, comprising the amino acid sequence from residue 67 to residue 115 of SEQ ID NO: 2 in which the cysteine residue at position 81 of SEQ ID NO: 2 is substituted with an amino acid other than cysteine.

4. The polypeptide of claim 3, wherein the amino acid other than cysteine is alanine.

5. The polypeptide of claim 1, comprising the amino acid sequence from residue 16 to residue 1I5 of SEQ ID NO: 2.

6. The polypeptide of claim 5, which has a disulfide bond between the cysteine residues at positions 95 and 112 of SEQ ID NO: 2.

7. The polypeptide of claim 5, which has disulfide bonds between the cysteine residues at positions 95 and 112 and positions 32 and 120 of SEQ ID NO: 2.

8. The polypeptide of claim 1, comprising the amino acid sequence from residue 1 to residue 115 of SEQ ID NO: 2.

9. The polypeptide of claim 8, which has disulfide bonds between the cysteine residues at positions 95 and 112 and positions 4 and 15 of SEQ ID NO: 2.

10. The polypeptide of claim 1, comprising the amino acid sequence from residue 67 to residue 126 of SEQ ID NO: 2.

11. The polypeptide of claim 10, which has a disulfide bond between the cysteine residues at positions 95 and 112 of SEQ ID NO: 2.

12. The polypeptide of claim 10, which has disulfide bonds between the cysteine residues at positions 4 and 15, positions 95 and 112, and positions 32 and 120 of SEQ ID NO: 2.

13. The polypeptide of claim 1, comprising the amino acid sequence from residue 16 to residue 126 of SEQ ID NO: 2.

14. The polypeptide of claim 1, comprising the amino acid sequence from residue 1 to residue 126 of SEQ ID NO: 2.

15. The polypeptide of claim 1, which inhibits the binding between von Willebrand factor and platelets.

16. The polypeptide of claim 15, which does not cause a substantial decrease in the number of platelets at a minimum dose for inhibiting the binding between von Willebrand factor and platelets when the polypeptide is administered in vivo.

17. An isolated and purified DNA fragment encoding the polypeptide of claim 1.

18. A recombinant vector comprising the DNA fragment of claim 17.

19. A host cell transformed with the recombinant vector of claim 18.

20. The transformed host cell of claim 19, which is *Escherichia coli*, a cultured insect cell or a cultured animal cell.

21. A method of producing the polypeptide of claim 1, comprising culturing the transformed host cell of claim 19 in a suitable culture medium to produce the polypeptide, followed by isolating the polypeptide from the culture medium.

22. A method of producing the monomeric polypeptide of claim 1 from a dimeric polypeptide which is obtainable from the venom of *Crotalus horridus horridus*, wherein the dimeric polypeptide has two polypeptide chains that are linked by at least one inter-chain disulfide bond, said method comprising:

exposing the multimeric polypeptide to a protein-denaturing agent and a reducing agent selected from the group consisting of glutathione and cysteine, thereby reducing the inter-chain disulfide bond to produce the monomeric polypeptide of claim 1, followed by isolating the monomeric polypeptide.

23. A method of producing the monomeric polypeptide of claim 1, comprising:

culturing *Escherichia coli* transformed with the vector of claim 1 in a suitable culture medium to accumulate the polypeptide in the *Escherichia coli*, exposing the polypeptide accumulated in the *Escherichia coli* to a protein-denaturing agent, followed by generating intra-molecular disulfide bonds within the chains of the polypeptide by removing the protein denaturing agent or by decreasing the concentration of the protein denaturing agent.

24. A pharmaceutical composition comprising a therapeutically effective amount of the polypeptide of claim 1 or a pharmaceutically acceptable salt of the polypeptide.

25. A method of inhibiting the binding between binding between von Willebrand factor and platelets in a patient in need thereof, comprising administering to the patient an effective amount of the polypeptide of claim 1.

26. A method of producing an anti-thrombus effect in a patient in need thereof, comprising administering to the patient an effective amount of the polypeptide of claim 1.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
( A ) LENGTH: 38 amino acids
( B ) TYPE: amino acid
( D ) TOPOLOGY: linear ( i i ) MOLECULE TYPE: peptide ( x i ) SEQUENCE DESCRIPTION: SEQ ID NO:1:

```
Asp Leu Glu Cys Pro Ser Gly Trp Ser Ser Tyr Asp Arg Tyr Cys Tyr
 1              5                  10                  15
Lys Pro Phe Lys Gln Glu Met Thr Trp Ala Asp Ala Glu Arg Phe Cys
            20                  25                  30
Ser Glu Gln Ala Lys Gly
        35
```

( 2 ) INFORMATION FOR SEQ ID NO:2:

( i ) SEQUENCE CHARACTERISTICS:
( A ) LENGTH: 126 amino acids
( B ) TYPE: amino acid
( D ) TOPOLOGY: linear ( i i ) MOLECULE TYPE: peptide ( x i ) SEQUENCE DESCRIPTION: SEQ ID NO:2:

```
Asp Leu Glu Cys Pro Ser Gly Trp Ser Ser Tyr Asp Arg Tyr Cys Tyr
 1              5                  10                  15
```

Lys Pro Phe Lys Gln Glu Met Thr Trp Ala Asp Ala Glu Arg Phe Cys
20 25 30

Ser Glu Gln Ala Lys Gly Gly His Leu Leu Ser Val Glu Thr Ala Leu
35 40 45

Glu Ala Ser Phe Val Asp Asn Val Leu Tyr Ala Asn Lys Glu Tyr Leu
50 55 60

Thr Arg Tyr Ile Trp Ile Gly Leu Arg Val Gln Asn Lys Gly Gln Pro
65 70 75 80

Cys Ser Ser Ile Ser Tyr Glu Asn Leu Val Asp Pro Phe Glu Cys Phe
85 90 95

Met Val Ser Arg Asp Thr Arg Leu Arg Glu Trp Phe Lys Val Asp Cys
100 105 110

Glu Gln Gln His Ser Phe Ile Cys Lys Phe Thr Arg Pro Arg
115 120 125

( 2 ) INFORMATION FOR SEQ ID NO:3:

( i ) SEQUENCE CHARACTERISTICS:
( A ) LENGTH: 21 amino acids
( B ) TYPE: amino acid
( D ) TOPOLOGY: linear ( i i ) MOLECULE TYPE: peptide ( x i ) SEQUENCE DESCRIPTION: SEQ ID NO:3:

Asp Cys Pro Ser Asp Trp Ser Ser Tyr Glu Gly His Cys Tyr Arg Val
1 5 10 15

Phe Gln Gln Glu Met
20

( 2 ) INFORMATION FOR SEQ ID NO:4:

( i ) SEQUENCE CHARACTERISTICS:
( A ) LENGTH: 17 bases
( B ) TYPE: nucleic acid
( C ) STRANDEDNESS: single
( D ) TOPOLOGY: linear ( i i ) MOLECULE TYPE: other..synthetic DNA ( i i i ) HYPOTHETICAL: NO ( i v ) ANTI-SENSE: NO ( x i ) SEQUENCE DESCRIPTION: SEQ ID NO:4:

CARGARATGA CNTGGGC 17

( 2 ) INFORMATION FOR SEQ ID NO:5:

( i ) SEQUENCE CHARACTERISTICS:
( A ) LENGTH: 17 bases
( B ) TYPE: nucleic acid
( C ) STRANDEDNESS: single
( D ) TOPOLOGY: linear ( i i ) MOLECULE TYPE: other..synthetic DNA ( i i i ) HYPOTHETICAL: NO ( i v ) ANTI-SENSE: YES ( x i ) SEQUENCE DESCRIPTION: SEQ ID NO:5:

TCNACYTTRA ACCAYTC 17

( 2 ) INFORMATION FOR SEQ ID NO:6:

(i) SEQUENCE CHARACTERISTICS:
(A) LENGTH: 272 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Crotalus horridus horridus
(B) STRAIN:

(xi) SEQUENCE DESCRIPTION: SEQ ID NO:6:

```
CAGGAGATGA CTTGGGCCGA TGCAGAGAGG TTCTGCTCGG AGCAGGCGAA GGGCGGGCAT    60

CTCCTCTCTG TCGAAACCGC CCTAGAAGCA TCCTTTGTGG ACAATGTGCT CTATGCGAAC   120

AAAGAGTACC TCACACGTTA TATCTGGATT GGACTGAGGG TTCAAAACAA AGGACAGCCA   180

TGCTCCAGCA TCAGTTATGA GAACCTGGTT GACCCATTTG AATGTTTTAT GGTGAGCAGA   240

GACACAAGGC TTCGTGAGTG GTTCAAAGTC GA                                 272
```

(2) INFORMATION FOR SEQ ID NO:7:

(i) SEQUENCE CHARACTERISTICS:
(A) LENGTH: 690 base pairs
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (vi) ORIGINAL SOURCE:
(A) ORGANISM: Crotalus horridus horridus
(B) STRAIN:

(ix) FEATURE:
(A) NAME/KEY: CDS
(B) LOCATION: 66..512

(xi) SEQUENCE DESCRIPTION: SEQ ID NO:7:

```
CTGAGCAGAC TTGCTACCTG TGGAGGCCGA GGAACAGTTC TCTCTGCAGG GAAGGAAAGA    60

ACGCC ATG GGG CGA TTC ATC TTC GTG AGC TTC AAC TTG CTG GTC GTG TTC   110
      Met Gly Arg Phe Ile Phe Val Ser Phe Asn Leu Leu Val Val Phe
        1               5                  10                  15

CTC TCC CTA AGT GGA ACT CTA GCT GAT TTG GAA TGT CCC TCC GGT TGG     158
Leu Ser Leu Ser Gly Thr Leu Ala Asp Leu Glu Cys Pro Ser Gly Trp
                20                  25                  30

TCT TCC TAT GAT CGG TAT TGC TAC AAG CCC TTC AAA CAA GAG ATG ACC     206
Ser Ser Tyr Asp Arg Tyr Cys Tyr Lys Pro Phe Lys Gln Glu Met Thr
            35                  40                  45

TGG GCC GAT GCA GAG AGG TTC TGC TCG GAG CAG GCG AAG GGC GGG CAT     254
Trp Ala Asp Ala Glu Arg Phe Cys Ser Glu Gln Ala Lys Gly Gly His
        50                  55                  60

CTC CTC TCT GTC GAA ACC GCC CTA GAA GCA TCC TTT GTG GAC AAT GTG     302
Leu Leu Ser Val Glu Thr Ala Leu Glu Ala Ser Phe Val Asp Asn Val
    65                  70                  75

CTC TAT GCG AAC AAA GAG TAC CTC ACA CGT TAT ATC TGG ATT GGA CTG     350
Leu Tyr Ala Asn Lys Glu Tyr Leu Thr Arg Tyr Ile Trp Ile Gly Leu
 80                  85                  90                  95
```

-continued

```
AGG GTT CAA AAC AAA GGA CAG CCA TGC TCC AGC ATC AGT TAT GAG AAC      398
Arg Val Gln Asn Lys Gly Gln Pro Cys Ser Ser Ile Ser Tyr Glu Asn
                100                 105                 110

CTG GTT GAC CCA TTT GAA TGT TTT ATG GTG AGC AGA GAC ACA AGG CTT      446
Leu Val Asp Pro Phe Glu Cys Phe Met Val Ser Arg Asp Thr Arg Leu
            115                 120                 125

CGT GAG TGG TTT AAA GTT GAC TGT GAA CAA CAA CAT TCT TTC ATA TGC      494
Arg Glu Trp Phe Lys Val Asp Cys Glu Gln Gln His Ser Phe Ile Cys
        130                 135                 140

AAG TTC ACG CGA CCA CGT TAAGATCCGG CTGTGTGAAG TCTGGAGAAG             542
Lys Phe Thr Arg Pro Arg
    145

CAAGGAAGCC CCCCACCTCT CCCCACCCCC CACCTTCCGC AATCTCTGCT CTTCCCCCTT    602

TGCTCAGTGG ATGCTCTCTG TAGCCGGATC TGGGTTTTCT GCTCCAGATG GGTCAGAAGA    662

TCCAATAAAT TCTGCCTACC CAAAAAAA                                       690
```

(2) INFORMATION FOR SEQ ID NO:8:

(i) SEQUENCE CHARACTERISTICS:
(A) LENGTH: 149 amino acids
(B) TYPE: amino acid
(D) TOPOLOGY: linear (ii) MOLECULE TYPE: peptide (xi) SEQUENCE DESCRIPTION: SEQ ID NO:8:

```
Met Gly Arg Phe Ile Phe Val Ser Phe Asn Leu Leu Val Val Phe Leu
  1               5                  10                  15

Ser Leu Ser Gly Thr Leu Ala Asp Leu Glu Cys Pro Ser Gly Trp Ser
             20                  25                  30

Ser Tyr Asp Arg Tyr Cys Tyr Lys Pro Phe Lys Gln Glu Met Thr Trp
         35                  40                  45

Ala Asp Ala Glu Arg Phe Cys Ser Glu Gln Ala Lys Gly Gly His Leu
     50                  55                  60

Leu Ser Val Glu Thr Ala Leu Glu Ala Ser Phe Val Asp Asn Val Leu
 65                  70                  75                  80

Tyr Ala Asn Lys Glu Tyr Leu Thr Arg Tyr Ile Trp Ile Gly Leu Arg
                 85                  90                  95

Val Gln Asn Lys Gly Gln Pro Cys Ser Ser Ile Ser Tyr Glu Asn Leu
            100                 105                 110

Val Asp Pro Phe Glu Cys Phe Met Val Ser Arg Asp Thr Arg Leu Arg
        115                 120                 125

Glu Trp Phe Lys Val Asp Cys Glu Gln Gln His Ser Phe Ile Cys Lys
    130                 135                 140

Phe Thr Arg Pro Arg
145
```

(2) INFORMATION FOR SEQ ID NO:9:

(i) SEQUENCE CHARACTERISTICS:
(A) LENGTH: 34 bases
(B) TYPE: nucleic acid
(C) STRANDEDNESS: single
(D) TOPOLOGY: linear (ii) MOLECULE TYPE: other..synthetic DNA (iii) HYPOTHETICAL: NO (iv) ANTI-SENSE: NO (xi) SEQUENCE DESCRIPTION: SEQ ID NO:9:

GGCGGCATAT GGATTTGGAA TGTCCCTCCG GTTG 34

(2) INFORMATION FOR SEQ ID NO:10:

(i) SEQUENCE CHARACTERISTICS:
(A) LENGTH: 40 bases
(B) TYPE: nucleic acid
(C) STRANDEDNESS: single
(D) TOPOLOGY: linear (ii) MOLECULE TYPE: other..synthetic DNA (iii) HYPOTHETICAL: NO (iv) ANTI-SENSE: YES (xi) SEQUENCE DESCRIPTION: SEQ ID NO:10:

TATCTCGAGA AGCTTACAGC CGGATCTTAA CGTGGTCGCG 40

(2) INFORMATION FOR SEQ ID NO:11:

(i) SEQUENCE CHARACTERISTICS:
(A) LENGTH: 26 bases
(B) TYPE: nucleic acid
(C) STRANDEDNESS: single
(D) TOPOLOGY: linear (ii) MOLECULE TYPE: other..synthetic DNA (iii) HYPOTHETICAL: NO (iv) ANTI-SENSE: NO (xi) SEQUENCE DESCRIPTION: SEQ ID NO:11:

GATGCTGGAG GCTGGCTGTC CTTTGT 26

(2) INFORMATION FOR SEQ ID NO:12:

(i) SEQUENCE CHARACTERISTICS:
(A) LENGTH: 26 bases
(B) TYPE: nucleic acid
(C) STRANDEDNESS: single
(D) TOPOLOGY: linear (ii) MOLECULE TYPE: other..synthetic DNA (iii) HYPOTHETICAL: NO (iv) ANTI-SENSE: YES (xi) SEQUENCE DESCRIPTION: SEQ ID NO:12:

GGACAGCCAG CCTCCAGCAT CAGTTA 26

(2) INFORMATION FOR SEQ ID NO:13:

(i) SEQUENCE CHARACTERISTICS:
(A) LENGTH: 35 bases
(B) TYPE: nucleic acid
(C) STRANDEDNESS: single
(D) TOPOLOGY: linear (ii) MOLECULE TYPE: other..synthetic DNA (iii) HYPOTHETICAL: NO (iv) ANTI-SENSE: YES (xi) SEQUENCE DESCRIPTION: SEQ ID NO:13:

GGTGGATCCA TATGTACAAG CCCTTCAAAC AAGAG 35

-continued ( 2 ) INFORMATION FOR SEQ ID NO:14:

( i ) SEQUENCE CHARACTERISTICS:
( A ) LENGTH: 36 bases
( B ) TYPE: nucleic acid
( C ) STRANDEDNESS: single
( D ) TOPOLOGY: linear ( i i ) MOLECULE TYPE: other..synthetic DNA ( i i i ) HYPOTHETICAL: NO ( i v ) ANTI-SENSE: NO ( x i ) SEQUENCE DESCRIPTION: SEQ ID NO:14:

CTCAGAAAGC TTTTATTGTT GTTCACAGTC AACTTT 36

( 2 ) INFORMATION FOR SEQ ID NO:15:

( i ) SEQUENCE CHARACTERISTICS:
( A ) LENGTH: 35 bases
( B ) TYPE: nucleic acid
( C ) STRANDEDNESS: single
( D ) TOPOLOGY: linear ( i i ) MOLECULE TYPE: other..synthetic DNA ( i i i ) HYPOTHETICAL: NO ( i v ) ANTI-SENSE: YES ( x i ) SEQUENCE DESCRIPTION: SEQ ID NO:15:

GGTGGATCCA TATGTATATC TGGATTGGAC TGAGG 35